(12) United States Patent
Wochner

(10) Patent No.: US 10,648,017 B2
(45) Date of Patent: May 12, 2020

(54) METHODS FOR RNA ANALYSIS

(71) Applicant: CureVac Real Estate GmbH, Tübingen (DE)

(72) Inventor: Aniela Wochner, Tübingen (DE)

(73) Assignee: CureVac Real Estate GmbH, Tübingen (DE)

( * ) Notice: Subject to any disclaimer, the term of this patent is extended or adjusted under 35 U.S.C. 154(b) by 519 days.

(21) Appl. No.: 15/195,901

(22) Filed: Jun. 28, 2016

(65) Prior Publication Data

US 2016/0304938 A1 Oct. 20, 2016

Related U.S. Application Data

(63) Continuation of application No. PCT/EP2014/003482, filed on Dec. 30, 2014.

(30) Foreign Application Priority Data

Dec. 30, 2013 (WO) .................. PCT/EP2013/003947

(51) Int. Cl.
*C12P 19/34* (2006.01)
*C12Q 1/6806* (2018.01)
*B01D 15/16* (2006.01)
*B01D 15/32* (2006.01)
*C07H 21/02* (2006.01)
*G01N 30/88* (2006.01)

(52) U.S. Cl.
CPC ......... *C12Q 1/6806* (2013.01); *B01D 15/163* (2013.01); *B01D 15/325* (2013.01); *C07H 21/02* (2013.01); *G01N 30/88* (2013.01); *G01N 2030/8827* (2013.01)

(58) Field of Classification Search
CPC ............ C12Q 1/6806; C12Q 2521/337; C12Q 2565/125; C12Q 2565/137; B01D 15/163; B01D 15/325; C07H 21/02; G01N 2030/8827; G01N 30/88
USPC ...................................................... 435/91.21
See application file for complete search history.

(56) References Cited

U.S. PATENT DOCUMENTS

| | | | |
|---|---|---|---|
| 7,074,596 B2 | 7/2006 | Darzynkiewicz et al. | |
| 2004/0077565 A1* | 4/2004 | Pavco | C12N 15/113 514/44 R |
| 2005/0032730 A1 | 2/2005 | Von der Mulbe et al. | |
| 2005/0059624 A1 | 3/2005 | Hoerr et al. | |
| 2005/0074760 A1* | 4/2005 | Matulic-Adamic | C07H 19/06 435/6.13 |
| 2005/0250723 A1 | 11/2005 | Hoerr et al. | |
| 2006/0188490 A1 | 8/2006 | Hoerr et al. | |
| 2008/0025944 A1 | 1/2008 | Hoerr et al. | |
| 2008/0267873 A1 | 10/2008 | Hoerr et al. | |
| 2009/0197336 A1* | 8/2009 | Farrar | A61K 48/005 435/455 |
| 2009/0324584 A1 | 12/2009 | Hoerr et al. | |
| 2010/0048883 A1 | 2/2010 | Ketterer et al. | |
| 2010/0189729 A1 | 7/2010 | Hoerr et al. | |
| 2010/0203076 A1 | 8/2010 | Fotin-Mleczek et al. | |
| 2010/0291156 A1 | 11/2010 | Barner et al. | |
| 2010/0305196 A1 | 12/2010 | Probst et al. | |
| 2011/0053829 A1 | 3/2011 | Baumhof et al. | |
| 2011/0250225 A1 | 10/2011 | Fotin-Mleczek et al. | |
| 2012/0021043 A1 | 1/2012 | Kramps et al. | |
| 2012/0258046 A1 | 10/2012 | Mutzke | |
| 2013/0129754 A1 | 5/2013 | Thess et al. | |
| 2013/0142818 A1 | 6/2013 | Baumhof et al. | |
| 2013/0259879 A1 | 10/2013 | Baumhof et al. | |
| 2013/0280283 A1 | 10/2013 | Lorenz et al. | |
| 2013/0295043 A1 | 11/2013 | Kallen et al. | |

(Continued)

FOREIGN PATENT DOCUMENTS

| | | |
|---|---|---|
| WO | WO 2016/091391 | 6/1916 |
| WO | WO 2016/097065 | 6/1916 |

(Continued)

OTHER PUBLICATIONS

Jemielity et al., "Novel anti-reverse cap analogs with superior translational properties," *RNA*, 9(9):1108-1122, 2003.

(Continued)

*Primary Examiner* — Cynthia B Wilder

(74) *Attorney, Agent, or Firm* — Parker Highlander PLLC

(57) ABSTRACT

The present invention relates to the field of RNA analysis. In particular, the invention concerns the use of a catalytic nucleic acid molecule for the analysis of an RNA molecule. The invention concerns methods for analyzing the 5' terminal structures of an RNA molecule having a cleavage site for a catalytic nucleic acid molecule. In particular, the invention concerns a method for determining the presence of a cap structure in an RNA molecule having a cleavage site for a catalytic nucleic acid molecule, a method for determining the capping degree of a population of RNA molecules having a cleavage site for a catalytic nucleic acid molecule, a method for determining the orientation of the cap structure in a capped RNA molecule having a cleavage site for a catalytic nucleic acid molecule and a method for determining relative amounts of correctly capped RNA molecules and reverse-capped RNA molecules in a population of RNA molecules, wherein the population comprises correctly capped and/or reverse-capped RNA molecules that have a cleavage site for a catalytic nucleic acid molecule. Moreover, the present invention provides uses of a catalytic nucleic acid molecule.

17 Claims, 14 Drawing Sheets

Specification includes a Sequence Listing.

(56) References Cited

U.S. PATENT DOCUMENTS

| | | |
|---|---|---|
| 2013/0336998 A1 | 12/2013 | Kallen et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | Von Der Mulbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |

FOREIGN PATENT DOCUMENTS

| | | |
|---|---|---|
| WO | WO 2016/107877 | 7/1916 |
| WO | WO 1996/040906 | 12/1996 |
| WO | WO 2000/070039 | 11/2000 |
| WO | WO 2001/079524 | 10/2001 |
| WO | WO 2008/077592 | 7/2008 |
| WO | WO 2012/135805 | 10/2012 |
| WO | WO 2014/152659 | 9/2014 |
| WO | WO 2014152659 * | 9/2014 |
| WO | WO 2015/149944 | 10/2015 |
| WO | WO 2017/001058 | 1/2017 |

OTHER PUBLICATIONS

Kore et al., "Synthesis and biological evaluation of trimethyl-substituted cap analogs," *Bioorganic & Medicinal Chemistry Letters*, 18(3):880-884, 2008.

Kore et al., "Synthesis and biological validation of N<7>-(4-chlorophenoxyethyl) substituted dinucleotide cap analogs for mRNA translation," *Bioorganic & Medicinal Chemistry*, 21(15):4570-4574, 2013.

Kore et al., "Synthesis and evaluation of 2'-O-allyl substituted dinucleotide cap analog for mRNA translation," *Bioorganic & Medicinal Chemistry*, 18(22):8061-8065, 2010.

McCall et al., "Small, efficient hammerhead ribozymes," *Molecular Biotechnology*, 14(1):5-17, 2000.

PCT International Search Report and Written Opinion issued in International Application No. PCT/EP2014/003482, dated Jun. 17, 2015.

Schubert et al., "Ribozyme- and deoxyribozyme-strategies for medical applications," *Current Drug Targets*, 5(8):667-681, 2004.

Singh et al., "Capping of mammalian U6 small nuclear RNA in vitro is directed by a conserved stem-loop and AUAUAC sequence: conversion of a noncapped RNA into a capped RNA," *Molecular and Cellular Biology*, 10(3):939-946, 1990.

Tcherepanova et al., "Ectopic expression of a truncated CD40L protein from synthetic post-transcriptionally capped RNA in dendritic cells induces high levels of IL-12 secretion," *BMC Molecular Biology*, 9(1):90, 2008.

Theus et al., "A simple assay for determining the capping efficiencies of RNA polymerases used for in vitro transcription," *Biotechniques*, 9(5):610-12, 614, 1990.

Campbell et al., "The effect of structure in a long target RNA on ribozyme cleavage efficiency," *Nucleic Acids Research*, 25(24):4985-4993, 1997.

Fukada et al., "A strategy for developing a hammerhead ribozyme for selective RNA cleavage depending on substitutional RNA editing," *RNA*, 18(9):1735-1744, 2012.

Office Action issued in European Application No. 148331309.9, dated Jan. 3, 2018.

Basturea, "Research Methods for Detection and Quantification of RNA Modifications", *Mater. Methods*, 3(186), 2013.

Cunningham, "New modalities in oncology: ribozymes", *BUMC Proc.*, 15:247-249, 2002.

Karikó et al., "Lipofectin-aided cell delivery of ribozyme targeted to human urokinase receptor mRNA", *FEBS Lett.*, 352:41-44, 1994.

Kashani-Sabet, "Ribozyme Therpeutics", *JID Symp. Proc.*, 7:76-78, 2002.

Khan, "Ribozyme: A clinical tool", *Clin. Chim. Acta*, 367:20-27, 2006.

Nakamura et al., "Design of Hammerhead Ribozymes that Cleave Murine Sry mRNA in vitro and in vivo", *J. Reprod. Dev.*, 52:73-80, 2006.

Notice of Opposition against corresponding European Patent No. 3090060, submitted to the European Patent Office dated Nov. 19, 2019.

Peng et al., "Synthesis and Application of a Chain-Terminating Dinucleotide mRNA Cap Analog", *Org. Lett.*, 4:161-164, 2002.

* cited by examiner

GGGAGAAAGCUUACCAUGCAGGCCGAGGGCCGCGGCACCGGCGGCUCGACC
GGCGACGCCGACGGGCCCGGCGGCCCGGGCAUCCCGGACGGCCCGGGCGGG
AACGCGGGCGGCCCGGGCGAGGCCGGCGCCACCGGCGGGCGGGGCCCGCGG
GGCGCCGGCGCCGCCCGGGCGAGCGGCCCCGGCGGGGGCGCCCCGCGGGGC
CCGCACGGCGGCGCCGCCAGCGGCCUGAACGGGUGCUGCCGGUGCGGCGCC
CGCGGCCCGGAGAGCCGGCUCCUGGAGUUCUACCUGGCCAUGCCG
UUCGCGACCCCGAUGGAGGCCGAGCUGGCCCGGCGGAGCCUGGCCCAGGAC
GCCCCGCCGCUGCCCGUGCCGGGCGUGCUCCUGAAGGAGUUCACGGUGAGC
GGCAACAUCCUGACCAUCCGGCUGACCGCCGCGGACCACCGGCAGCUGCAG
CUGUCGAUCAGCAGCUGCCUCCAGCAGCUGAGCCUGCUGAUGUGGAUCACC
CAGUGCUUCCUGCCGGUGUUCCUGGCCCAGCCGCCCAGCGGCCAGCGCCGG
UGACCACUAGUUAUAAGACUGACUAGCCCGAUGGGCCUCCCAACG
GGCCCUCCUCCCCUCCUUGCACCGAGAUUAAUAAAAAAAAAAAAAAAAAA
AAAAAAAAAAAAAAAAAAAAAAAAAAAAAAAAAAAAAAAAAAAAUGCAUC
CCCCCCCCCCCCCCCCCCCCCCCCCCCCCCAAAGGCUCUUUCAGAGCCAC
CAGAAUU

Fig. 1

```
GGGAGAAAGCUUACCAUGGAGGACGCCAAGAACAUCAAGAAGGGCCCGGCGCCCU
UCUACCCGCUGGAGGACGGGACCGCCGGCGAGCAGCUCCACAAGGCCAUGAAGCG
GUACGCCCUGGUGCCGGGCACGAUCGCCUUCACCGACGCCCACAUCGAGGUCGAC
AUCACCUACGCGGAGUACUUCGAGAUGAGCGUGCGCCUGGCCGAGGCCAUGAAGC
GGUACGGCCUGAACACCAACCACCGGAUCGUGGUGUGCUCGGAGAACAGCCUGCA
GUUCUUCAUGCCGGUGCUGGGCGCC
CUCUUCAUCGGCGUGGCCGUCGCCCCGGCGAACGACAUCUACAACGAGCGGGAGC
UGCUGAACAGCAUGGGGAUCAGCCAGCCGACCGUGGUGUUCGUGAGCAAGAAGGG
CCUGCAGAAGAUCCUGAACGUGCAGAAGAAGCUGCCCAUCAUCCAGAAGAUCAUC
AUCAUGGACAGCAAGACCGACUACCAGGGCUUCCAGUCGAUGUACACGUUCGUGA
CCAGCCACCUCCCGCCGGGCUUCAACGAGUACGACUUCGUCCCGGAGAGCUUCGA
CCGGGACAAGACCAUCGCCCUGAUC
AUGAACAGCAGCGGCAGCACCGGCCUGCCGAAGGGGGUGGCCCUGCCGCACCGGA
CCGCCUGCGUGCGCUUCUCGCACGCCCGGGACCCCAUCUUCGGCAACCAGAUCAU
CCCGGACACCGCCAUCCUGAGCGUGGUGCCGUUCCACCACGGCUUCGGCAUGUUC
ACGACCCUGGGCUACCUCAUCUGCGGCUUCCGGGUGGUCCUGAUGUACCGGUUCG
AGGAGGAGCUGUUCCUGCGGAGCCUGCAGGACUACAAGAUCCAGAGCGCGCUGCU
CGUGCCGACCCUGUUCAGCUUCUUC
GCCAAGAGCACCCUGAUCGACAAGUACGACCUGUCGAACCUGCACGAGAUCGCCA
GCGGGGGCGCCCCGCUGAGCAAGGAGGUGGGCGAGGCCGUGGCCAAGCGGUUCCA
CCUCCCGGGCAUCCGCCAGGGCUACGGCCUGACCGAGACCACGAGCGCGAUCCUG
AUCACCCCCGAGGGGGACGACAAGCCGGGCGCCGUGGGCAAGGUGGUCCCGUUCU
UCGAGGCCAAGGUGGUGGACCUGGACACCGGCAAGACCCUGGGCGUGAACCAGCG
GGGCGAGCUGUGCGUGCGGGGCCCG
AUGAUCAUGAGCGGCUACGUGAACAACCCGGAGGCCACCAACGCCCUCAUCGACA
AGGACGGCUGGCUGCACAGCGGCGACAUCGCCUACUGGGACGAGGACGAGCACUU
CUUCAUCGUCGACCGGCUGAAGUCGCUGAUCAAGUACAAGGGCUACCAGGUGGCG
CCGGCCGAGCUGGAGAGCAUCCUGCUCCAGCACCCCAACAUCUUCGACGCCGGCG
UGGCCGGGCUGCCGGACGACGACGCCGGCGAGCUGCCGGCCGCGGUGGUGGUGCU
GGAGCACGGCAAGACCAUGACGGAG
AAGGAGAUCGUCGACUACGUGGCCAGCCAGGUGACCACCGCCAAGAAGCUGCGGG
GCGGCGUGGUGUUCGUGGACGAGGUCCCGAAGGGCCUGACCGGGAAGCUCGACGC
CCGGAAGAUCCGCGAGAUCCUGAUCAAGGCCAAGAAGGGCGGCAAGAUCGCCGUG
UGAGGACUAGUUAUAAGACUGACUAGCCCGAUGGGCCUCCCAACGGGCCCUCCUC
CCCUCCUUGCACCGAGAUUAAUAAAAAAAAAAAAAAAAAAAAAAAAAAAAAAAAA
AAAAAAAAAAAAAAAAAAAAAAAA
AAAAAAUGCAUCCCCCCCCCCCCCCCCCCCCCCCCCCCCCAAAGGCUCUUUUC
AGAGCCACCAGAAUU
```

Fig. 2

```
GGGAGAAAGCUUACCAUGAAGGCCGUGCUGCUCGCGCUGCUGAUGGCCGGC
CUGGCCCUGCAGCCGGGGACCGCCCUGCUGUGCUACAGCUGCAAGGCCCAG
GUCUCGAACGAGGACUGCCUGCAGGUGGAGAACUGCACGCAGCUGGGCGAG
CAGUGCUGGACCGCCCGGAUCCGCGCCGUGGGCCUGCUCACCGUGAUCAGC
AAGGGCUGCAGCCUGAACUGCGUGGACGACAGCCAGGACUACUACGUGGGC
AAGAAGAACAUCACCUGCUGCGACACCGACCUGUGCAACGCCAGC
GGCGCCCACGCCCUGCAGCCCGCGGCCGCCAUCCUGGCCCUGCUGCCCGCC
CUGGGCCUGCUGCUCUGGGGCCCCGGCCAGCUGUGACCACUAGUUAUAAGA
CUGACUAGCCCGAUGGGCCUCCCAACGGGCCCUCCUCCCCUCCUUGCACCG
AGAUUAAUAAAAAAAAAAAAAAAAAAAAAAAAAAAAAAAAAAAAAAAAAA
AAAAAAAAAAAAAAAAAAAAUGCAUCCCCCCCCCCCCCCCCCCCCCCC
CCCCCAAGGCUCUUUCAGAGCCACCAGAAUU
```

Fig. 3

A
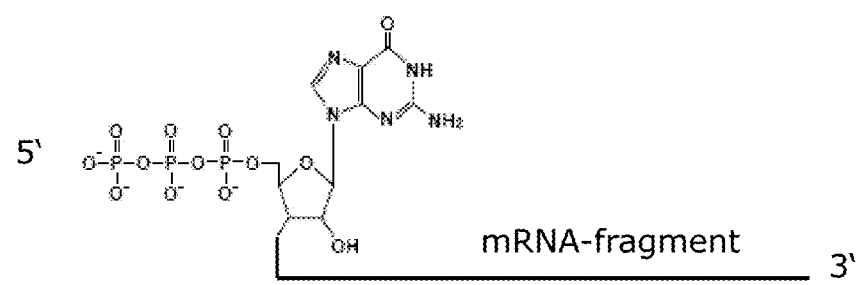
B
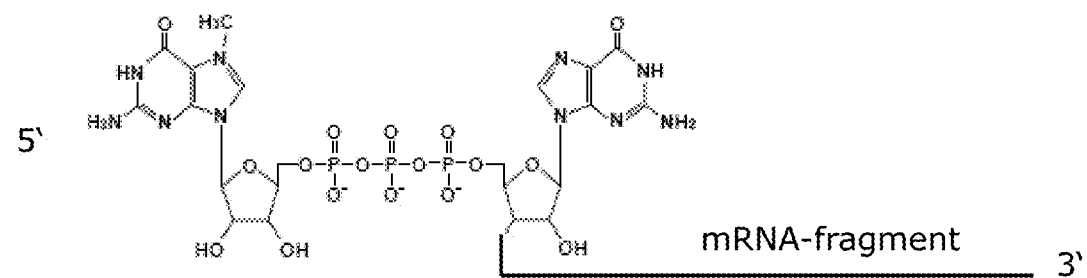
Figs. 4A-B

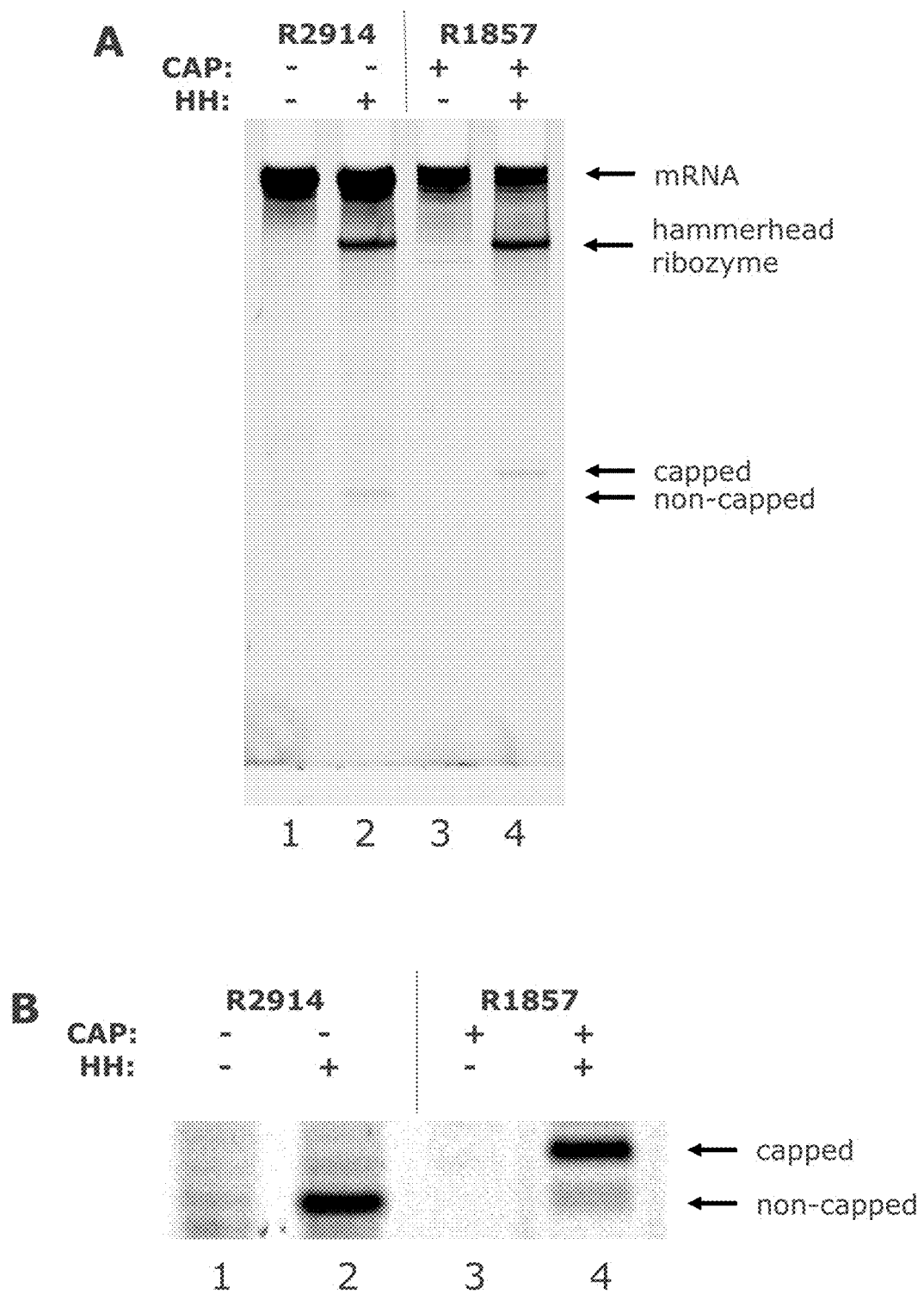
Figs. 7A-B

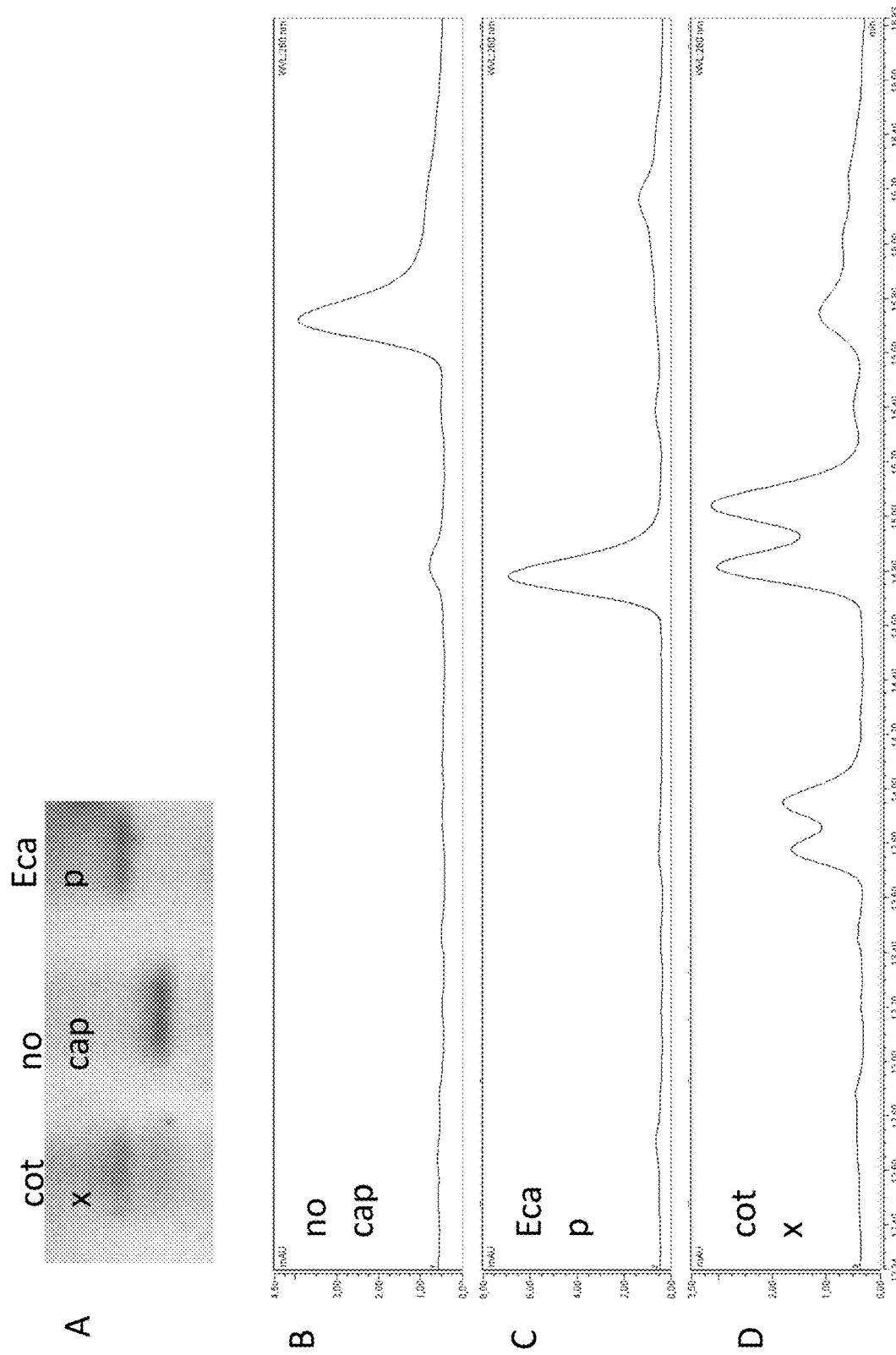
Figs. 9A-D

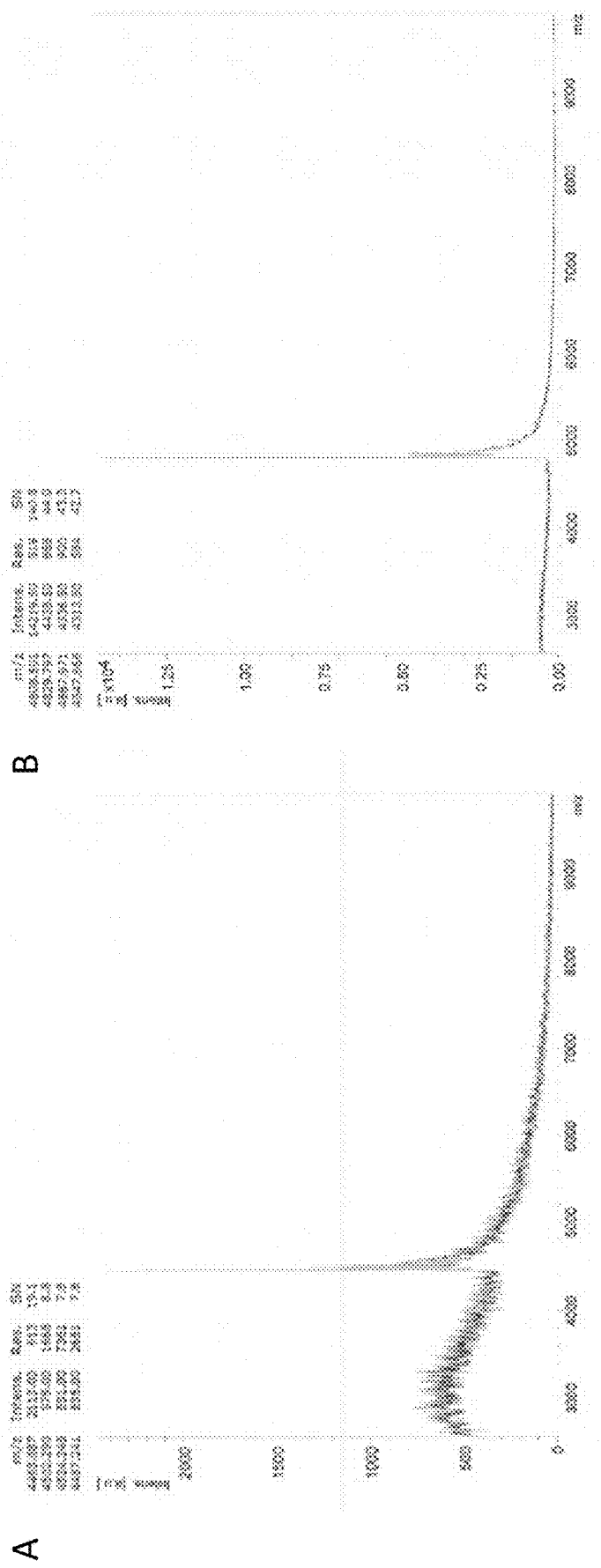
Figs. 11A-B

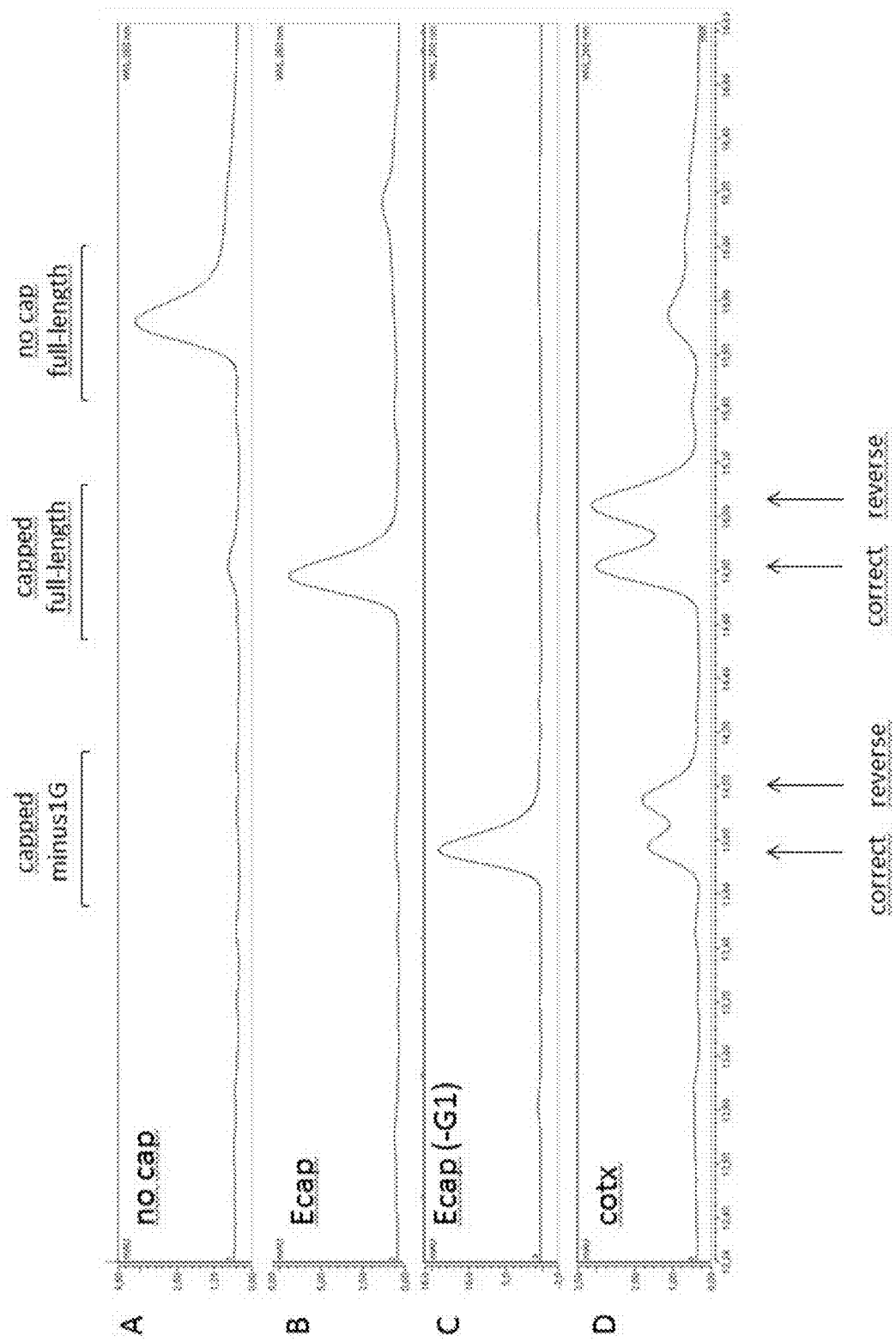
Figs. 12A-D

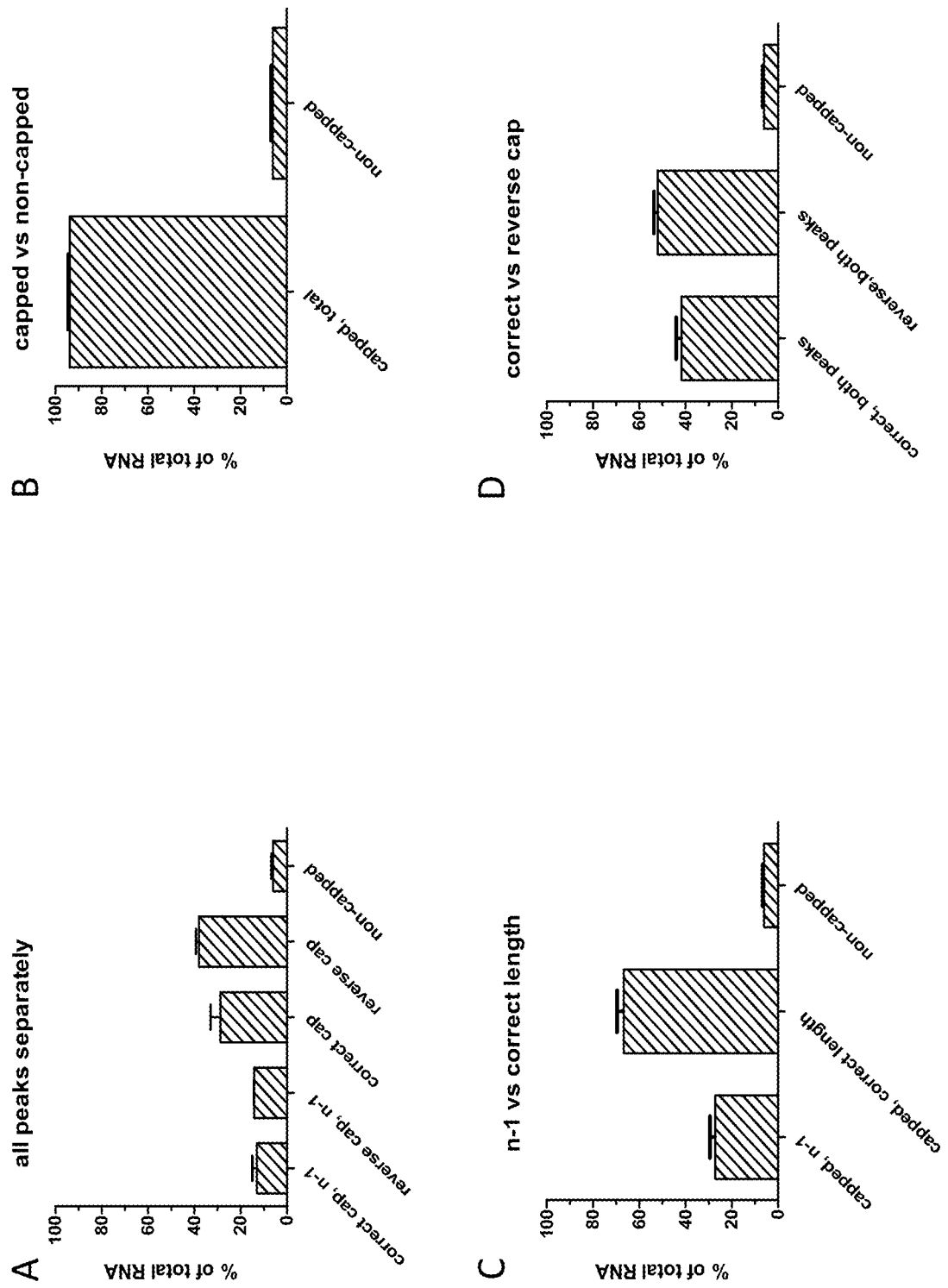
Figs. 13A-D

SEQUENCE LISTING

```
<160> NUMBER OF SEQ ID NOS: 6

<210> SEQ ID NO 1
<211> LENGTH: 53
<212> TYPE: RNA
<213> ORGANISM: Artificial Sequence
<220> FEATURE:
<223> OTHER INFORMATION: hammerhead ribozyme RNA
<220> FEATURE:
<221> NAME/KEY: misc_feature
<222> LOCATION: (1)..(7)
<223> OTHER INFORMATION: n is a, c, g, or u
<220> FEATURE:
<221> NAME/KEY: misc_feature
<222> LOCATION: (15)..(38)
<223> OTHER INFORMATION: n is a, c, g, or u
<220> FEATURE:
<221> NAME/KEY: misc_feature
<222> LOCATION: (43)..(53)
<223> OTHER INFORMATION: n is a, c, g, or u
```

<400> SEQUENCE: 1
nnnnnnncug augannnnnn nnnnnnnnnn nnnnnnnnga aannnnnnnn nnn    53

<210> SEQ ID NO 2
<211> LENGTH: 52
<212> TYPE: RNA
<213> ORGANISM: Artificial Sequence
<220> FEATURE:
<223> OTHER INFORMATION: hammerhead ribozyme HHNUH2d

<400> SEQUENCE: 2
gcauggcuga ugaggccucg accgauaggu cgaggccgaa aagcuuucuc cc    52

<210> SEQ ID NO 3
<211> LENGTH: 760
<212> TYPE: RNA
<213> ORGANISM: Homo sapiens

<400> SEQUENCE: 3
gggagaaagc uuaccaugca ggccgagggc cgcggcaccg gcggcucgac cggcgacgcc    60
gacgggcccg gcggcccggg caucccggac ggcccgggcg ggaacgcggg cggcccgggc    120
gaggccggcg ccaccggcgg gcggggcccg cggggcgccg gcgccgcccg gcgagcggc    180 cccggcgggg gcgccccgcg gggcccgcac ggcggcgccg ccagcggccu gaacggguc    240 ugccggugcg gcgcccgcgg cccggagagc cggcuccugg aguucuaccu ggccaugccg    300
uucgcgaccc cgauggaggc cgagcuggcc cggcggagcc uggccaggac gccccgccg    360 cugcccgugc cgggcgugcu ccugaaggag uucacggugga gcggcaacau ccugaccauc    420
cggcugaccg ccgcggacca ccggcagcug cagcugucga ucagcagcug ccuccagcag    480
cugagccugc ugaugugggau cacccagugc uuccugccgg uguccuggc ccagccgccc    540 agcggccagc gccggugacc acuaguuaua agacugacua gcccgauggg ccucccaacg    600 ggccccuccuc cccuccuugc accgagauua auaaaaaaa aaaaaaaaaa aaaaaaaaa    660 aaaaaaaaa aaaaaaaaa aaaaaaaaa aaaaaugca ucccccccc cccccccc    720 cccccccc ccaaaggcuc uuuucagagc caccagaauu    760

<210> SEQ ID NO 4
<211> LENGTH: 1870
<212> TYPE: RNA
<213> ORGANISM: Artificial Sequence
<220> FEATURE:
<223> OTHER INFORMATION: PpLuc - Photinus pyralis Luciferase

<400> SEQUENCE: 4
gggagaaagc uuaccaugga ggacgccaag aacaucaaga agggcccggc gcccuucuac    60
ccgcuggagg acgggaccgc cggcgagcag cuccacaagg ccaugaagcg guacgcccug    120
gugccgggca cgaucgccuu caccgacgcc cacaucgagg ucgacaucac cuacgcggag    180
uacuucgaga ugagcgugcg ccuggccgag gccaugaagc gguacggccu gaacaccaac    240
caccggaucg uggugugcuc ggagaacagc cugcaguucu ucaugccggu gcugggcgcc    300
cucuucaucg gcguggccgu cgccccgcgc aacgacaucu acaacgagcg ggagcugcug    360
aacagcaugg ggaucagcca gccgaccgug guguucgug gcaagaaggg ccugcagaag    420
auccugaacg ugcagaagaa gcugcccauc uccagaga ucaucaucau ggacagcaag    480
accgacuacc agggcuucca gucgauguac acguucguga ccagccaccu cccgccgggc    540

| | |
|---|---|
| uucaacgagu acgacuucgu cccggagagc uucgaccggg acaagaccau cgcccugauc | 600 |
| augaacagca gcggcagcac cggccugccg aaggggguggg cccugccgca ccggaccgcc | 660 |
| ugcgugcgcu ucucgcacgc ccgggacccc aucuucggca accagaucau cccggacacc | 720 |
| gccauccuga gcguggugcc guuccaccac ggcuucggca guucacgac ccugggcuac | 780 |
| cucaucugcg gcuuccgggu gguccugaug uaccgguucg aggaggagcu guccugcgg | 840 |
| agccugcagg acuacaagau ccagagcgcg cugcucgugc cgacccuguu cagcuucuuc | 900 |
| gccaagagca cccugaucga caaguacgac cugucgaacc ugcacgagau cgccagcggg | 960 |
| ggcgccccgc ugagcaagga gguggggcgag gccguggcca agcgguucca ccucccgggc | 1020 |
| auccgccagg gcuacggccu gaccgagacc acgagcgcga uccugaucac ccccgagggg | 1080 |
| gacgacaagc cggcgccgu gggcaaggug gucccguucu ucgaggccaa ggugguggac | 1140 |
| cuggacaccg gcaagacccu gggcgugaac cagcggggcg agcugugcgu gcggggggccg | 1200 |
| augaucauga gcggcuacgu gaacaaccccg gaggccacca acgcccucau cgacaaggac | 1260 |
| ggcuggcugc acagcggcga caucgccuac ugggacgagg acgagcacuu cuucaucguc | 1320 |
| gaccggcuga agucgcugau caaguacaag ggcuaccagg uggcgccggc cgagcuggag | 1380 |
| agcauccugc uccagcaccc caacaucuuc gacgccggcg uggccgggcu gccggacgac | 1440 |
| gacgccggcg agcugccggc cgcgguggug gugcuggagc acggcaagac caugacggag | 1500 |
| aaggagaucu cgacuacgu ggccagccag gugaccaccg ccaagaagcu gcggggcggc | 1560 |
| guggugcuucg uggacgaggu cccgaagggc cugaccggga agcucgacgc ccggaagauc | 1620 |
| cgcgagaucc ugaucaaggc caagaagggc ggcaagaucg ccgugugagg acuaguuaua | 1680 |
| agacugacua gcccgauggg ccucccaacg ggccuccuc cccuccuugc accgagauua | 1740 |
| auaaaaaaaa aaaaaaaaaa aaaaaaaaaa aaaaaaaaaa aaaaaaaaaa aaaaaaaaaa | 1800 |
| aaaaaaugca uccccccccc cccccccccc cccccccccc ccaaaggcuc uuuucagagc | 1860 |
| caccagaauu | 1870 |

<210> SEQ ID NO 5
<211> LENGTH: 589
<212> TYPE: RNA
<213> ORGANISM: Homo sapiens

<400> SEQUENCE: 5

| | |
|---|---|
| gggagaaagc uuaccaugaa ggccgugcug cucgcgcugc ugauggccgg ccuggcccug | 60 |
| cagccgggga ccgccugcu gugcuacagc ugcaaggccc aggucucgaa cgaggacugc | 120 |
| cugcaggugg agaacugcac gcagcugggc gagcagcu ggaccgcccg gauccgcgcc | 180 |
| gugggccugc ucaccgugau cagcaagggc ugcagccuga acugcgugga cgacagccag | 240 |
| gacuacuacg ugggcaagaa gaacaucacc ugcugcgaca ccgaccugug caacgccagc | 300 |
| ggcgccacg cccugcagcc cgcggccgcc auccuggccc ugcugccgc ccugggccug | 360 |
| cugcucuggg gccccggcca gcugugacca cuaguuauaa gacugacuag cccgauggc | 420 |
| cucccaacgg gccuccucc ccuccuugca ccgagauuaa uaaaaaaaaa aaaaaaaaaa | 480 |
| aaaaaaaaaa aaaaaaaaaa aaaaaaaaaa aaaaaaaaaa aaaaaugcau cccccccccc | 540 |
| cccccccccc cccccccccc caaaggcucu uuucagagcc accagaauu | 589 |

<210> SEQ ID NO 6
<211> LENGTH: 10
<212> TYPE: DNA
<213> ORGANISM: Artificial Sequence

```
<220> FEATURE:
<223> OTHER INFORMATION: 5' terminal sequence

<400> SEQUENCE: 6
gggagaaagc                                                                    10
```

METHODS FOR RNA ANALYSIS

This application is a continuation of International Application No. PCT/EP2014/003482, filed Dec. 30, 2014, which claims priority to European Application No. PCT/EP2013/003947, filed Dec. 30, 2013, the entirety of each of which is incorporated herein by reference.

The present invention relates to the field of RNA analysis. In particular, the invention concerns the use of a catalytic nucleic acid molecule for the analysis of an RNA molecule. In one aspect, the invention concerns methods for analyzing the 5' terminal structures of an RNA molecule having a cleavage site for a catalytic nucleic acid molecule. In particular, the invention concerns a method for determining the presence of a cap structure in an RNA molecule having a cleavage site for a catalytic nucleic acid molecule, a method for determining the capping degree of a population of RNA molecules having a cleavage site for a catalytic nucleic acid molecule, a method for determining the orientation of the cap structure in a capped RNA molecule having a cleavage site for a catalytic nucleic acid molecule and a method for determining relative amounts of correctly capped RNA molecules and reverse-capped RNA molecules in a population of RNA molecules, wherein the population comprises correctly capped and/or reverse-capped RNA molecules that have a cleavage site for a catalytic nucleic acid molecule. Moreover, the present invention provides uses of a catalytic nucleic acid molecule. In particular, the invention relates to the use of a catalytic nucleic acid molecule in a method for determining the presence of a cap structure in an RNA molecule, the use of a catalytic nucleic acid molecule in a method for determining the capping degree of a population of RNA molecules, the use of a catalytic nucleic acid molecule in a method for determining the orientation of the cap structure in a capped RNA molecule and in a method for determining the relative amounts of correctly capped RNA molecules and reverse-capped RNA molecules in a population of RNA molecules. Furthermore, the present invention provides a 5' terminal RNA fragment obtainable by the methods according to the invention. In addition, an RNA molecule is provided, which comprises a cap structure at its 5' terminus and the sequence motif NUH as defined herein at its 3' terminus. Further, the invention also relates to uses of the 5' terminal RNA fragment and the RNA molecule.

The present invention relates inter alia to a method of determining the capping degree of a population of RNA molecules having a cleavage site for a catalytic nucleic acid molecule, comprising the steps of:
a) providing a sample containing the population of RNA molecules,
b) cleaving the RNA molecules with the catalytic nucleic acid molecule into a 5' terminal RNA fragment and at least one 3' RNA fragment by contacting the sample with the catalytic nucleic acid molecule under conditions allowing the cleavage of the RNA molecules,
c) separating the RNA fragments obtained in step b),
d) determining a measure for the amount of the capped and non-capped 5' terminal RNA fragments separated in step c) of said population of RNA molecules, and
e) comparing said measures of capped and non-capped 5' terminal RNA fragments determined in step d), thereby determining the capping degree of said population of RNA molecules.

Furthermore the invention provides the use of a catalytic nucleic acid molecule for determining the capping degree of a population of RNA molecules, particularly in the quality control of the production process of nucleic acids, particularly of RNA.

Therapeutic RNA molecules represent an emerging class of drugs. RNA-based therapeutics include mRNA molecules encoding antigens for use as vaccines. mRNA vaccines combine desirable immunological properties with the flexibility of genetic vaccines. In addition, mRNA is considered to be a safer vector than DNA-based vectors because RNA cannot integrate into genomic DNA possibly leading to insertional mutagenesis. In addition, it is envisioned to use mRNA therapeutics for replacement therapies, e.g. providing missing proteins such as growth factors or enzymes to patients (Schlake et al., 2012. RNA Biol. 9(11):1319-30).

Successful protein expression from transfected RNA depends on transfection efficiency, RNA stability and translation efficiency. The 5' cap structure and the 3' poly(A) tail are important features for the efficient translation of mRNA and protein synthesis in eukaryotic cells. Newly synthesized mRNAs are usually modified within the producing cell with a 5' cap structure when the transcript reaches a length of 20 to 30 nucleotides. First, the 5' terminal nucleotide pppN is converted to 5' GpppN by a bi-functional capping enzyme containing both RNA 5'-triphosphatase and guanylyltransferase activities. Then the GpppN part is methylated by a second enzyme with (guanine-7)-methyltransferase activity to form the monomethylated m7GpppN type 0 cap structure. The type 0 cap is then converted to an m7GpppN type 1 structure in the nucleus by 2'-O-methylation (Tcherepanova et al., 2008. BMC Mol. Biol. 9:90).

Short RNA molecules can be synthesized by chemical methods, whereas long RNAs are typically produced by in vitro transcription using suitable DNA templates with a promoter and RNA polymerases, for example bacteriophage T3 or T7 RNA polymerases. In principle, 5' cap structures can be introduced into in vitro transcribed RNA by using one of two protocols.

In the first protocol, capping occurs concurrently with the initiation of transcription (co-transcriptional capping). In this approach, a dinucleotide cap analog such as m7G(5')ppp(5')G (m7G) is added to the reaction mixture. The DNA template is usually designed in such a way that the first nucleotide transcribed is a guanosine. The cap analog directly competes with GTP for incorporation as initial nucleotide and is incorporated as readily as any other nucleotide (WO2006/004648). A molar excess of the cap analog relative to GTP facilitates the incorporation of the cap dinucleotide at the first position of the transcript. However, this approach always yields a mixture of capped and uncapped RNAs. Uncapped mRNAs can usually not be translated after transfection into eukaryotic cells, thus reducing the efficacy of the RNA therapeutic.

The effective concentration of co-transcriptionally capped mRNAs with the standard cap analog (m7GpppG) is further reduced because the analog can be incorporated in the reverse orientation (Gpppm7G), which is less competent for translation (Stepinski et al., 2001. RNA 7(10):1486-95). The issue of cap analog orientation can be solved by using anti-reverse cap analogs (ARCA) such as (3'-O-methyl)GpppG which cannot be incorporated in the reverse orientation (Grudzien et al., 2004. RNA 10(9):1479-87).

In the second protocol, capping is done in a separate enzymatic reaction after in vitro transcription (post-transcriptional or enzymatic capping). Vaccinia Virus Capping Enzyme (VCE) possesses all three enzymatic activities necessary to synthesize a m7G cap structure (RNA 5'-triphosphatase, ganylyltransferase, and guanine-7-methyltransferase). Using GTP as substrate the VCE reaction yields RNA caps in the correct orientation. In addition, a type 1 cap can be created by adding a second Vaccinia enzyme, 2' O methyltransferase, to the capping reaction (Tcherepanova et al., 2008. BMC Mol. Biol. 9:90).

Accordingly, the 5' cap structure is an important feature for the efficient translation of RNA molecules and protein synthesis in eukaryotic cells. The presence of non-capped RNA molecules may reduce the translation efficiency of a population of RNA molecules and should therefore be avoided or at least reduced. Therefore it is important to determine the capping degree of a population of RNA molecules. Since also the orientation of the cap structure at the 5' terminus of an RNA may influence, for example, its translation, it is also necessary to determine the orientation of the cap structure in an RNA molecule.

For the therapeutic use of RNA in patients a rigorous quality control of the synthetic RNA is mandatory. For example, the capping degree needs to be monitored for each production batch because the capping degree influences the stability and translational efficiency and thus the pharmacokinetic and pharmacodynamic properties of the RNA therapeutic. Several approaches were described for the determination of capping degrees including gel shift assays and RNaseH cleavage assays.

For the characterization of novel cap analogs and the determination of the capping degree of short in vitro transcripts a gel shift assay was reported (Kore et al., 2008. Bioorg. Med. Chem. Lett. 18(3):880-4). In the in vitro transcription reaction only ATP (including $\alpha$-$^{32}$P ATP for radioactive labeling) and GTP were used whereas CTP and UTP were omitted. Therefore, only six nucleotides at the 5' end were transcribed by T7 RNA polymerase. This setup produces a transcript of short enough length to distinguish via denaturing gel electrophoresis whether the cap or regular guanosine was incorporated. Capped RNAs migrate more slowly than uncapped RNAs, allowing the determination of the relative incorporation of cap versus unmodified G. As the gel shift assay requires single nucleotide resolution to distinguish capped from non-capped RNA, this method is limited to the analysis of short RNA molecules.

To measure the percentage of capped RNA in a population of long RNA molecules, an oligonucleotide-directed RNaseH cleavage assay was described (Tcherepanova et al., 2008. BMC Mol. Biol. 9:90). A DNA oligonucleotide was annealed in proximity to the 5' end of the RNA molecule such that the size of the digested products was 19 nucleotides long for non-capped and 20 nucleotides long for capped RNA molecules. The digested fragments were radiolabeled and separated by polyacrylamide gel electrophoresis (PAGE) and visualized by autoradiography. The interpretation of the resulting band pattern was complicated by the presence of an additional band in the uncapped RNA lane possibly resulting from "RNA-oligo hybrid breathing" or altered conformation due to the absence of a cap structure. Thus it needs to be assured that the RNaseH cleaves precisely at the intended position and that the cleavage reaction proceeds completely which may require further optimization of the reaction conditions for individual oligonucleotide-RNA pairs.

In view of the above, there is a continued need for novel analytical methods to assess the quality of RNA, and especially the capping degree of RNA, particularly of long RNA molecules.

It is thus one of the objectives of the present invention to provide a method for analyzing RNA. In particular, a method shall be provided, which is suitable for use in quality control during or following production of RNA, especially of RNA, which is intended to be used in diagnostic or therapeutic environments. Furthermore, it is an objective of the present invention to provide a method for analyzing a mixture of RNA molecules or an RNA population.

SUMMARY OF THE INVENTION

The present invention relates, inter alia, to a method for analyzing an RNA molecule having a cleavage site for a catalytic nucleic acid molecule, the method comprising the steps of:
  a) providing an RNA molecule having a cleavage site for a catalytic nucleic acid molecule,
  b) cleaving the RNA molecule with the catalytic nucleic acid molecule into a 5' terminal RNA fragment and at least one 3' RNA fragment by contacting the RNA molecule with the catalytic nucleic acid molecule under conditions allowing the cleavage of the RNA molecule,
  c) determining a physical property of the RNA molecule by analyzing the 5' terminal RNA fragment.

In a preferred embodiment, the method according to the invention comprises analyzing the 5' terminus, a 5' terminal modification or a 5' terminal fragment of an RNA molecule. Preferably, the method for analyzing an RNA molecule according to the invention comprises determining the presence or absence of a 5' cap structure at the 5' terminus of an RNA molecule. Further, the method may comprise determining the orientation of a cap structure at the 5' terminus of an RNA molecule.

In another preferred embodiment, the method according to the invention comprises the analysis of a population of RNA molecules. Therein, the method preferably comprises determining the relative amounts of RNA molecules having distinct physical properties, such as the relative amount of capped RNA molecules, the relative amount of correctly capped RNA molecules or the relative amount of RNA molecules having a specific structural feature at the 5' terminus.

In a preferred embodiment, the present invention relates to a method of determining the capping degree of a population of RNA molecules having a cleavage site for a catalytic nucleic acid molecule, comprising the steps of:
  a) providing a sample containing the population of RNA molecules,
  b) cleaving the RNA molecules with the catalytic nucleic acid molecule into a 5' terminal RNA fragment and at least one 3' RNA fragment by contacting the sample with the catalytic nucleic acid molecule under conditions allowing the cleavage of the RNA molecules,
  c) separating the RNA fragments obtained in step b),
  d) determining a measure for the amount of the capped and non-capped 5' terminal RNA fragments separated in step c) of said population of RNA molecules, and
  e) comparing said measures of capped and non-capped 5' terminal RNA fragments determined in step d), thereby determining the capping degree of said population of RNA molecules.

In another aspect, the present invention further provides a novel use of a catalytic nucleic acid molecule for analyzing an RNA molecule as further defined herein.

In addition, the invention provides an RNA molecule consisting of 10 to 20 nucleotides, wherein the RNA molecule comprises a cap structure at its 5' terminus and the sequence NUH at its 3' terminus, wherein N is selected from G, A, C and U, and H is selected from A, C and U. A 5' terminal fragment is further provided, which is obtainable by the methods described herein. The invention also relates to the uses of the RNA molecule or the 5' terminal fragment as defined herein.

Definitions

For the sake of clarity and readability the following definitions are provided. Any technical feature mentioned for these definitions may be read on each and every embodiment of the invention. Additional definitions and explanations may be specifically provided in the context of these embodiments as discussed and explained further below.

Population of RNA molecules: In the context of the present invention, the phrases "population of RNA molecules" or "RNA population" refers to a plurality of RNA molecules comprising at least one RNA molecule having a cleavage site for a catalytic nucleic acid molecule. Preferably, the at least one RNA molecule having a cleavage site for a catalytic nucleic acid molecule is characterized by a distinct property or a structural feature, which may be determined by the method according to the invention. In addition to the at least one RNA molecule having a cleavage site for a catalytic nucleic acid molecule, the population may optionally further comprise at least one other RNA molecule that does not have such a cleavage site for a catalytic nucleic acid molecule. In one embodiment, a population of RNA molecules may be a plurality of identical RNA molecules having a cleavage site for a catalytic nucleic acid molecule. In another embodiment, a population of RNA molecules comprises at least two distinct RNA molecules having a cleavage site for a catalytic nucleic acid molecule. In that embodiment, the two distinct RNA molecules are distinct from each other with regard to at least one distinct physical property or structural feature as defined herein. In a preferred embodiment, a "population of RNA molecules" in the context of the present invention, comprises at least two distinct RNA molecules having a cleavage site for a catalytic nucleic acid molecule, wherein the at least two distinct RNA molecules differ from each other only in one physical property or only in one structural feature, which is preferably located close to the 5' terminus of the RNA molecules, and wherein the distinct physical property or the structural feature as defined herein may be determined by the method according to the invention.

In a preferred embodiment, the phrase "population of RNA molecules" refers to a plurality of RNA molecules, which have, apart from the cap molecule present on some RNA molecules, the same nucleotide sequence. In other words, the population of RNA molecules comprises a plurality of capped and non-capped RNA molecules having the identical nucleotide sequence with the exception of the presence of a cap structure at the 5' end of capped RNA molecules. According to the invention, said RNA molecules of the population contain a cleavage site for a catalytic nucleic acid molecule, allowing the cleavage of the RNA molecules into fragments, which can then be separated and detected. In this context, said RNA molecules can be isolated RNA molecules.

In a further preferred embodiment, the phrase "population of RNA molecules" refers to a plurality of RNA molecules, wherein at least RNA molecule is capped and has a cleavage site for a catalytic nucleic acid molecule and wherein the orientation of the cap may be determined by the method according to the invention.

Catalytic nucleic acid molecule: By "catalytic nucleic acid molecule" it is meant a nucleic acid molecule capable of catalyzing reactions including, but not limited to, site-specific cleavage of other nucleic acid molecules.

In a preferred embodiment, the term "catalytic nucleic acid molecule" means a nucleic acid molecule with endonuclease activity. Such a molecule with endonuclease activity may have complementarity in a substrate binding region to a specified binding site in a nucleic acid target, and also has an enzymatic activity that specifically cleaves RNA or DNA in that target at a specific cleavage site. Therefore, the nucleic acid molecule with endonuclease activity is able to intramolecularly (in cis) or intermolecularly (in trans) cleave RNA or DNA. This complementarity functions to allow sufficient hybridization of the catalytic nucleic acid molecule to the target RNA or DNA and thereby allowing the cleavage of the target RNA or DNA at a specific cleavage site. In this context, 100% complementarity in the substrate binding region of the catalytic nucleic acid molecule to the binding site of the nucleic acid target is preferred, but complementarity of at least 50%, of at least 60%, of at least 70%, more preferably of at least 80 or 90% and most preferably of at least 95% may also be useful in this invention. The catalytic nucleic acid molecule may contain modified nucleotides, which may be modified at the base, sugar, and/or phosphate groups. The term catalytic nucleic acid is used interchangeably with phrases such as enzymatic nucleic acid or nucleic acid enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule is that it has a specific substrate binding region which is complementary to one or more binding sites of the target nucleic acid, and that it has nucleotide sequences within or surrounding that substrate binding region which impart a nucleic acid cleaving activity to the molecule. The term "catalytic nucleic acid molecule" includes ribozymes and DNAzymes as defined below.

Ribozyme: A ribozyme is a catalytic nucleic acid molecule which is an RNA molecule capable of catalyzing reactions including, but not limited to, site-specific cleavage of other nucleic acid molecules such as RNA molecules. The term ribozyme is used interchangeably with phrases such as catalytic RNA, enzymatic RNA, or RNA enzyme.

In the early 80s natural RNA molecules were discovered which are capable of catalyzing reactions in the absence of any protein component and these molecules were named ribozymes. Several classes of ribozymes occurring in natural systems have been discovered, most of which catalyse intramolecular splicing or cleavage reactions (reactions 'in cis'). Since most of the naturally occurring ribozymes catalyse self-splicing or self-cleavage reactions, it was necessary to convert them into RNA enzymes which can cleave or modify target RNAs without becoming altered themselves (reactions 'in trans').

Ribozymes are broadly grouped into two classes based on their size and reaction mechanisms: large and small ribozymes. The first group consists of the self-splicing group I and group II introns as well as the RNA component of RNase P, whereas the latter group includes the hammerhead, hairpin, hepatitis delta ribozymes and varkud satellite (VS) RNA as well as artificially selected nucleic acids. Large ribozymes consist of several hundreds up to 3000 nucleotides and they generate reaction products with a free 3'-hydroxyl and 5'-phosphate group. In contrast, small catalytically active nucleic acids from 30 to ~150 nucleotides in length generate products with a 2'-3'-cyclic phosphate and a 5'-hydroxyl group (Schubert and Kurreck, 2004. Curr. Drug Targets 5(8):667-681).

Group I introns include the self-splicing intron in the pre-ribosomal RNA of the ciliate *Tetrahymena thermophilia*. Further examples of group I introns interrupt genes for rRNAs, tRNAs and mRNAs in a wide range of organelles and organisms. Group I introns perform a splicing reaction by a two-step transesterification mechanism: The reaction is initiated by a nucleophilic attack of the 3'-hydroxyl group of an exogenous guanosine cofactor on the 5'-splice site. Subsequently, the free 3'-hydroxyl of the upstream exon performs a second nucleophilic attack on the 3'-splice site to ligate both exons and release the intron. Substrate specificity of group I introns is achieved by an Internal Guide Sequence (IGS). The catalytically active site for the transesterification reaction resides in the intron, which can be re-engineered to catalyse reactions in trans.

Group II introns are found in bacteria and in organellar genes of eukaryotic cells. They catalyse a self-splicing reaction that is mechanistically distinct from group I introns because they do not require a guanosine cofactor. Instead, the 2'-hydroxyl of a specific adenosine at the so-called branch site of the intron initiates the reaction by a nucleophilic attack on the splice-site to form a lariat-type structure.

RNase P was the first example of a catalytic RNA that acts in trans on multiple substrates. RNase P can be considered to be the only true naturally occurring trans-cleaving RNA enzyme known to date. However, for full enzymatic activity under in vivo conditions the protein component is essential.

The hammerhead ribozyme is found in several plant virus satellite RNAs, viroids and transcripts of a nuclear satellite DNA of newt. This ribozyme is the smallest of the naturally occurring ribozymes and processes the linear concatamers that are generated during the rolling circle replication of circular RNA plant pathogens. The development of hammerhead variants that cleave target RNA molecules in trans was a major advancement that made possible the use of ribozyme technology for practical applications. The hammerhead ribozyme motif that has widely been applied since then comprises three helical sections connected via a three-way helical junction.

In hairpin ribozymes the catalytic entity is part of a four-helix junction. A minimal catalytic motif containing approximately 50 nucleotides has been identified that can be used for metal-ion dependent cleavage reactions in trans. It consists of two domains, each harbouring two helical regions separated by an internal loop, connected by a hinge region. One of these domains results from the association of 14 nucleotides of a substrate RNA with the ribozyme via base-pairing.

The hepatitis delta virus (HDV) ribozyme is found in a satellite virus of hepatitis B virus. Both the genomic and the antigenomic strand express cis-cleaving ribozymes of ~85 nucleotides that differ in sequence but fold into similar secondary structures. The crystal structure of the ribozyme reveals five helical regions are organized by two pseudoknot structures. The catalytic mechanism of the hepatitis delta virus ribozyme appears to involve the action of a cytosine base within the catalytic centre as a general acid-base catalyst. The hepatitis delta ribozyme displays high resistance to denaturing agents like urea or formamide. Trans-cleaving derivatives of this ribozyme have been developed.

The Varkud Satellite (VS) ribozyme is a 154 nucleotide long and is transcribed from a plasmid discovered in the mitochondria of certain strains of *Neurospora*. The VS ribozyme is the largest of the known nucleolytic ribozymes.

DNAzyme: A DNAzyme is a catalytic nucleic acid molecule which is a DNA molecule capable of catalyzing reactions including, but not limited to, site-specific cleavage of other nucleic acid molecules such as RNA molecules. The term DNAzyme is used interchangeably with phrases such as catalytic DNA, enzymatic DNA, or DNA enzyme.

DNAzymes are intrinsically more stable than ribozymes made of RNA. Although DNAzymes have not been found in nature, artificial DNAzymes such as "10-23" DNAzymes have been obtained by using in vitro selection methods (Schubert and Kurreck, 2004. Curr. Drug Targets 5(8):667-681).

One of the most active DNAzymes is the RNA-cleaving "10-23" DNAzyme which was generated by an in vitro selection method (Santoro et al., 1997. Proc. Natl. Acad. Sci. USA 94(9):4262-6). 10-23 DNAzymes consist of a catalytic core of about 15 nucleotides and two substrate binding arms of variable length and sequence. The 10-23 DNAzyme cleaves its RNA substrate using divalent ions to yield a 2'-3'-cyclo phosphate and a free 5'-hydroxyl group.

10-23 DNAzymes can be designed and used to cleave almost any target RNA in a sequence-specific manner. Consisting of a catalytic core of 15 nucleotides and two substrate-binding arms of variable length and sequence, they bind the target RNA in a sequence-specific manner and cleave it between a paired pyrimidine base and a free purine base (Schubert et al., 2003. Nucleic Acids Res. 31(20):5982-92). For example, the DNAzyme cleavage reaction can be performed by incubating the DNAzyme and the substrate RNA in cleavage buffer (10 mM MgCl$_2$, 50 mM Tris-HCl, pH7.5) at 37° C. Prior to mixing the enzyme and the substrate RNA, both solutions are denatured separately for 5 minutes at 85° C. Methods for the production of DNAzymes are known in the art. For example, DNAzymes can be chemically synthesized using standard DNA synthesis methods (Schubert et al., 2003. Nucleic Acids Res. 31(20):5982-92).

5'-Cap structure: A 5' cap is typically a modified nucleotide, particularly a guanine nucleotide, added to the 5' end of an RNA molecule. Preferably, the 5' cap is added using a 5'-5'-triphosphate linkage. A 5' cap may be methylated, e.g. m7GpppN, wherein N is the terminal 5' nucleotide of the nucleic acid carrying the 5' cap, typically the 5'-end of an RNA. The naturally occurring 5' cap is m7GpppN.

Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3' phosphorothioate, phosphorodithioate, or bridging or non-bridging methylphosphonate moiety.

Particularly preferred 5' cap structures are CAP1 (methylation of the ribose of the adjacent nucleotide of m7G), CAP2 (methylation of the ribose of the $2^{nd}$ nucleotide downstream of the m7G), CAP3 (methylation of the ribose of the $3^{rd}$ nucleotide downstream of the m7G), CAP4 (methylation of the ribose of the $4^{th}$ nucleotide downstream of the m7G), A 5' cap structure may be formed by a Cap analog.

Cap analog: A cap analog refers to a non-extendable di-nucleotide that has cap functionality which means that it facilitates translation or localization, and/or prevents degradation of the RNA molecule when incorporated at the 5' end of the RNA molecule. Non-extendable means that the cap analog will be incorporated only at the 5' terminus because it does not have a 5' triphosphate and therefore cannot be extended in the 3' direction by a template-dependent RNA polymerase. Cap analogs include, but are not limited to, a chemical structure selected from the group consisting of m7GpppG, m7GpppA, m7GpppC; unmethylated cap analogs (e.g., GpppG); dimethylated cap analog (e.g., m2,7GpppG), trimethylated cap analog (e.g., m2,2,7GpppG), dimethylated symmetrical cap analogs (e.g., m7Gpppm7G), or anti reverse cap analogs (e.g., ARCA; m7,2'OmeGpppG, m7,2'dGpppG, m7,3'OmeGpppG, m7,3'dGpppG and their tetraphosphate derivatives) (Stepinski et al., 2001. RNA 7(10):1486-95).

Examples of cap analogs are shown in Table 1.

TABLE 1

Cap analogs (D1 and D2 denote counterpart diastereoisomers)

| Triphosphate cap analog | Tetraphosphate cap analog |
|---|---|
| $m^7Gp_3G$ | $m^7Gp_4G$ |
| $m_2^{7,3'-O}Gp3G$ | $b^7Gp_4G$ |
| $b^7Gp_3G$ | $b^7m^{3'-O}Gp_4G$ |
| $e^7Gp_3G$ | $m_2^{2,7}Gp_4G$ |
| $m_2^{2,7}Gp_3G$ | $m_3^{2,2,7}Gp_4G$ |
| $m_3^{2,2,7}Gp_3G$ | $b^7m^2Gp_4G$ |
| $m^7Gp_32'dG$ | $m7Gp^4m^7G$ |
| $m^7Gp_3m^{2'-O}G$ | |
| $m^7Gp_3m^7G$ | |
| $m_2^{7,2'-O}Gp_3G$ | |
| $m_2^{7,2'-O}GpppsG$ (D1) | |
| $m_2^{7,2'-O}GpppsG$ (D2) | |
| $m_2^{7,2'-O}GppspG$ (D1) | |
| $m_2^{7,2'-O}GppspG$ (D2) | |
| $m_2^{7,2'-O}GpsppG$ (D1) | |
| $m_2^{7,2'-O}GpsppG$ (D2) | |

Further cap analogs have been described previously (U.S. Pat. No. 7,074,596, WO2008/016473, WO2008/157688, WO2009/149253, WO2011/015347, and WO2013/059475). The synthesis of $N^7$-(4-chlorophenoxyethyl) substituted dinucleotide cap analogs has been described recently (Kore et al., 2013. Bioorg. Med. Chem. 21(15):4570-4).

Particularly preferred cap analogs are G[5']ppp[5']G, $m^7G$ [5']ppp[5']G, $m_3^{2,2,7}$G[5']ppp[5']G, $m_2^{7,3',-O}$G[5']ppp[5']G (3'-ARCA), $m_2^{7,2'-O}$GpppG (2'-ARCA), $m_2^{7,2'-O}$GppspG D1 (β-S-ARCA D1) and $m_2^{7,2'-O}$GppspG D2 (β-S-ARCA D2).

Nucleic acid: The term nucleic acid means any DNA- or RNA-molecule and is used synonymous with polynucleotide. Furthermore, modifications or derivatives of the nucleic acid as defined herein are explicitly included in the general term "nucleic acid". For example, peptide nucleic acid (PNA) is also included in the term "nucleic acid".

Monocistronic RNA: A monocistronic RNA may typically be an RNA, preferably an mRNA, that comprises only one open reading frame. An open reading frame in this context is a sequence of several nucleotide triplets (codons) that can be translated into a peptide or protein.

Bi-/multicistronic RNA: RNA, preferably mRNA, that typically may have two (bicistronic) or more (multicistronic) open reading frames (ORF). An open reading frame in this context is a sequence of several nucleotide triplets (codons) that can be translated into a peptide or protein.

Nucleotide analogs: Nucleotide analogs are nucleotides structurally similar (analog) to naturally occurring nucleotides which include phosphate backbone modifications, sugar modifications, or modifications of the nucleobase.

Nucleic acid synthesis: Nucleic acid molecules used according to the invention as defined herein may be prepared using any method known in the art, including synthetic methods such as e.g. solid phase synthesis, in vivo propagation (e.g. in vivo propagation of viruses), as well as in vitro methods, such as in vitro transcription reactions.

For preparation of a nucleic acid molecule, especially if the nucleic acid is in the form of an RNA or mRNA, a corresponding DNA molecule may e.g. be transcribed in vitro. This DNA template preferably comprises a suitable promoter, e.g. a T7 or SP6 promoter, for in vitro transcription, which is followed by the desired nucleotide sequence coding for the nucleic acid molecule, e.g. mRNA, to be prepared and a termination signal for in vitro transcription. The DNA molecule, which forms the template of the at least one RNA of interest, may be prepared by fermentative proliferation and subsequent isolation as part of a plasmid which can be replicated in bacteria. Plasmids which may be mentioned as suitable for the present invention are e.g. the plasmids pT7Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

RNA: RNA is the usual abbreviation for ribonucleic acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA-sequence.

Messenger RNA (mRNA): In eukaryotic cells, transcription is typically performed inside the nucleus or the mitochondria. In vivo, transcription of DNA usually results in the so-called premature RNA which has to be processed into so-called messenger RNA, usually abbreviated as mRNA. Processing of the premature RNA, e.g. in eukaryotic organisms, comprises a variety of different posttranscriptional modifications such as splicing, 5'-capping, polyadenylation, export from the nucleus or the mitochondria and the like. The sum of these processes is also called maturation of mRNA. The mature messenger RNA usually provides the nucleotide sequence that may be translated into an amino acid sequence of a particular peptide or protein. Typically, a mature mRNA comprises a 5' cap, a 5'UTR, an open reading frame, a 3'UTR and a poly(A) sequence. In the context of the present invention, an mRNA may also be an artificial molecule, i.e. a molecule not occurring in nature. This means that the mRNA in the context of the present invention may, e.g., comprise a combination of a 5'UTR, open reading frame, 3'UTR and poly(A) sequence, which does not occur in this combination in nature.

Self-replicating RNA (Replicons): Self-replicating RNA are delivery vectors based on alphaviruses which have been developed from Semliki Forest virus (SFV), Sindbis (SIN) virus, and Venezuelan equine encephalitis (VEE) virus. Alphaviruses are single stranded RNA viruses in which heterologous genes of interest may substitute for the alphavirus' structural genes. By providing the structural genes in trans, the replicon RNA is packaged into replicon particles (RP) which may be used for gene therapy purposes or genetic vaccination (see for example Vander Veen et al., 2012. Alphavirus replicon vaccines. Animal Health Research Reviews, p. 1-9). After entry into the host cell, the genomic viral RNA initially serves as an mRNA for translation of the viral nonstructural proteins (nsPs) required for initiation of viral RNA amplification. RNA replication occurs via synthesis of a full-length minusstrand intermediate that is used as the template for synthesis of additional genome-length RNAs and for transcription of a plus-strand subgenomic RNA from an internal promoter. Such RNA may then be considered as self-replicating RNA, since the non-structural proteins responsible for replication (and transcription of the heterologous genes) are still present in such replicon. Such alphavirus vectors are referred to as "replicons."

Replicon particle: A replicon particle consist of two or three parts: i) the genetic material (=the replicon) (comprising viral genes and optional substituted heterologous genes) made from either DNA or RNA; ii) a protein coat that protects these genes; and in some cases iii) an envelope of lipids that surrounds the protein coat when they are outside a cell.

Sequence of a nucleic acid molecule: The sequence of a nucleic acid molecule is typically understood to be the particular and individual order, i.e. the succession of its nucleotides.

Sequence identity: Two or more sequences are identical if they exhibit the same length and order of nucleotides or amino acids. The percentage of identity typically describes the extent to which two sequences are identical, i.e. it typically describes the percentage of nucleotides that correspond in their sequence position with identical nucleotides of a reference-sequence. For determination of the degree of identity, the sequences to be compared are considered to exhibit the same length, i.e. the length of the longest sequence of the sequences to be compared. This means that a first sequence consisting of 8 nucleotides is 80% identical to a second sequence consisting of 10 nucleotides comprising the first sequence. In other words, in the context of the present invention, identity of sequences preferably relates to the percentage of nucleotides of a sequence which have the same position in two or more sequences having the same length. Gaps are usually regarded as non-identical positions, irrespective of their actual position in an alignment.

Fragment of a sequence: A fragment of a sequence is typically a shorter portion of a full-length sequence of e.g. a nucleic acid sequence or an amino acid sequence. Accordingly, a fragment of a sequence, typically, consists of a sequence that is identical to the corresponding stretch or corresponding stretches within the full-length sequence. A preferred fragment of a sequence in the context of the present invention, consists of a continuous stretch of entities, such as nucleotides or amino acids, corresponding to a continuous stretch of entities in the molecule the fragment is derived from, which represents at least 5%, preferably at least 20%, preferably at least 30%, more preferably at least 40%, more preferably at least 50%, even more preferably at least 60%, even more preferably at least 70%, and most preferably at least 80% of the total (i.e. full-length) molecule from which the fragment is derived. It is particularly preferred that the fragment of a sequence is a functional fragment, i.e. that the fragment fulfils one or more of the functions fulfilled by the sequence the fragment is derived from.

Fragments of nucleic acids: "Fragments" of nucleic acid sequences in the context of the present invention may comprise a sequence of a nucleic acid as defined herein, which is, with regard to its nucleic acid molecule 5'-, 3'- and/or intrasequentially truncated compared to the nucleic acid molecule of the original (native) nucleic acid molecule. A sequence identity with respect to such a fragment as defined herein may therefore preferably refer to the entire nucleic acid as defined herein.

Transfection: The term 'transfection' refers to the introduction of nucleic acid molecules, such as DNA or RNA (e.g. mRNA) molecules, into cells, preferably into eukaryotic cells. In the context of the present invention, the term 'transfection' encompasses any method known to the skilled person for introducing nucleic acid molecules, preferably RNA molecules, into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc.

Open reading frame: An open reading frame (ORF) in the context of the invention may typically be a sequence of several nucleotide triplets which may be translated into a peptide or protein. An open reading frame preferably contains a start codon, i.e. a combination of three subsequent nucleotides coding usually for the amino acid methionine (ATG or AUG), at its 5'-end and a subsequent region which usually exhibits a length which is a multiple of 3 nucleotides. An ORF is preferably terminated by a stop codon (e.g., TAA, TAG, TGA). Typically, this is the only stop codon of the open reading frame. Thus, an open reading frame in the context of the present invention is preferably a nucleotide sequence, consisting of a number of nucleotides that may be divided by three, which starts with a start codon (e.g. ATG or AUG) and which preferably terminates with a stop codon (e.g., TAA, TGA, or TAG or UAA, UAG, UGA, respectively). The open reading frame may be isolated or it may be incorporated in a longer nucleic acid sequence, for example in a vector or an mRNA. An open reading frame may also be termed "protein coding region" or "coding region".

5'-untranslated region (5'-UTR): A 5'-UTR is typically understood to be a particular section of messenger RNA (mRNA). It is located 5' of the open reading frame of the mRNA. Typically, the 5'-UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites. The 5'-UTR may be post-transcriptionally modified, for example by addition of a 5' cap structure. In the context of the present invention, the term "5'-UTR" typically refers to the sequence of an mRNA, which is located between the 5' cap structure and the start codon. Preferably, the 5'-UTR is the sequence, which extends from a nucleotide located 3' to the 5' cap structure, preferably from the nucleotide located immediately 3' to the 5' cap structure, to a nucleotide located 5' to the start codon of the protein coding region (or ORF), preferably to the nucleotide located immediately 5' to the start codon of the protein coding region.

DETAILED DESCRIPTION OF THE INVENTION

In a first aspect, the present invention relates to a method for analyzing an RNA molecule having a cleavage site for a catalytic nucleic acid molecule. In particular, the invention relates to a method for analyzing an RNA molecule having a cleavage site for a catalytic nucleic acid molecule, the method comprising the steps of:
  a) providing an RNA molecule having a cleavage site for a catalytic nucleic acid molecule,
  b) cleaving the RNA molecule with the catalytic nucleic acid molecule into a 5' terminal RNA fragment and at least one 3' RNA fragment by contacting the RNA molecule with the catalytic nucleic acid molecule under conditions allowing the cleavage of the RNA molecule,
  c) determining a physical property of the RNA molecule by analyzing the 5' terminal RNA fragment.

It has been found by the inventors that the generation of 5' terminal fragments by using a catalytic nucleic acid molecule and subsequent determination of a physical property of said fragment is particularly useful in methods typically employed in quality control of RNA having a cleavage site for the catalytic nucleic acid molecule. Advantageously, the method according to the invention allows specific and rapid analysis of RNA molecules during or following RNA production, preferably RNA production by in vitro transcription.

In general, the method according to the invention is not limited with respect to the type of RNA molecule to be analyzed. Preferably, the RNA molecule having a cleavage site for a catalytic nucleic acid molecule is an RNA molecule as defined herein. For example, the RNA molecule to be analyzed may be an single-stranded or a double-stranded RNA, preferably, without being limited thereto, an RNA oligonucleotide (oligoribonucleotide), preferably a short oligonucleotide, a coding RNA, a messenger RNA (mRNA), an immunostimulatory RNA, a ribosomal RNA (rRNA), a transfer RNA (tRNA), a viral RNA (vRNA), a self-replicating RNA (replicon), a small interfering RNA (siRNA), a microRNA, a small nuclear RNA (snRNA), a small-hairpin (sh) RNA or riboswitch, a ribozyme, or an aptamer. Preferably the RNA molecule is a primary microRNA (pri-miRNA) molecule. It is known that miRNAs are first transcribed as a largely unstructured precursor, termed a primary miRNA (pri-miRNA), which is sequentially processed in the nucleus, to give the approximately 65-nt pre-miRNA hairpin intermediate, and then in the cytoplasm, to give the mature miRNA. These pre-miRNA molecules can be capped and polyadenylated (Cai et al., 2004. RNA 10(12):1957-66).

Further preferably, the RNA molecule having a cleavage site for the catalytic nucleic acid molecule comprises at least one open reading frame (ORF) encoding at least one peptide or protein. More preferably, the RNA molecule is a (linear) single-stranded RNA, even more preferably an mRNA or an immunostimulatory RNA. In the context of the present invention, an mRNA is typically an RNA, which is composed of several structural elements, e.g. an optional 5' terminal cap structure, an optional 5'-UTR region, an upstream positioned ribosomal binding site followed by a coding region (open reading frame, ORF), an optional 3'-UTR region, which may be followed by a poly-A tail, a poly-C-tail, and/or a histone stem-loop sequence. An mRNA may occur as a mono-, di-, or even multicistronic RNA, i.e. an RNA, which carries the coding sequences of one, two or more proteins or peptides. Such coding sequences in di-, or even multicistronic mRNA may be separated by at least one IRES sequence, e.g. as defined herein.

In a preferred embodiment of the invention, the inventive method is for analyzing an RNA molecule having a cleavage site for a catalytic nucleic acid molecule, wherein the RNA molecule comprises at least one modification. In the context of the invention, an RNA molecule having at least one modification is also referred to as "modified RNA molecule". Therein, the modification is not limited to any particular structure. Preferably, the structural modification is a structural feature that is typically not found in the respective naturally occurring RNA, but is preferably introduced in an artificial RNA molecule, preferably in an artificial mRNA molecule. Several RNA modifications are known in the art, which can be applied to a given RNA in the context of the present invention. In the following, some exemplary modifications are described.

Chemical Modifications:

The term "RNA modification" as used herein may refer to chemical modifications comprising backbone modifications as well as sugar modifications or base modifications.

In this context, the modified RNA molecule as defined herein may contain nucleotide analogues/modifications, e.g. backbone modifications, sugar modifications or base modifications. A backbone modification in connection with the present invention is a modification, in which phosphates of the backbone of the nucleotides contained in an RNA molecule as defined herein are chemically modified. A sugar modification in connection with the present invention is a chemical modification of the sugar of the nucleotides of the RNA molecule as defined herein. Furthermore, a base modification in connection with the present invention is a chemical modification of the base moiety of the nucleotides of the RNA molecule. In this context, nucleotide analogues or modifications are preferably selected from nucleotide analogues which are applicable for transcription and/or translation.

Sugar Modifications:

The modified nucleosides and nucleotides, which may be incorporated into the modified RNA as described herein, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), -O(CH2CH2o)nCH2CH2OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH2; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified RNA can include nucleotides containing, for instance, arabinose as the sugar.

Backbone Modifications:

The phosphate backbone may further be modified in the modified nucleosides and nucleotides, which may be incorporated into the modified RNA, as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications:

The modified nucleosides and nucleotides, which may be incorporated into the modified RNA, as described herein, can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

In further specific embodiments the modified RNA may comprise nucleoside modifications selected from 6-aza-cytidine, 2-thio-cytidine, α-thio-cytidine, Pseudo-iso-cytidine, 5-aminoallyluridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytidine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, α-thio-adenosine, 8-azido-adenosine, 7-deazaadenosine.

Lipid Modification:

According to a further embodiment, the modified RNA as defined herein can contain a lipid modification. Such a lipid-modified RNA typically comprises an RNA as defined herein. Such a lipid-modified RNA molecule as defined herein typically further comprises at least one linker covalently linked with that RNA molecule, and at least one lipid covalently linked with the respective linker. Alternatively, the lipid-modified RNA molecule comprises at least one RNA molecule as defined herein and at least one (bifunctional) lipid covalently linked (without a linker) with that RNA molecule. According to a third alternative, the lipid-modified RNA molecule comprises an RNA molecule as defined herein, at least one linker covalently linked with that RNA molecule, and at least one lipid covalently linked with the respective linker, and also at least one (bifunctional) lipid covalently linked (without a linker) with that RNA molecule. In this context, it is particularly preferred that the lipid modification is present at the terminal ends of a linear RNA sequence.

Modification of the 5'-End of the Modified RNA:

According to another preferred embodiment of the invention, the modified RNA molecule as defined herein, can be modified by the addition of a so-called "5' CAP" structure. A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. m7Gppp(N) (wherein "N" is the first transcribed nucleotide) is the 5'-cap structure, which naturally occurs in mRNA transcribed by polymerase II and is therefore not considered as modification comprised in the modified RNA according to the invention. This means the modified RNA according to the present invention may comprise a m7Gppp (N) as 5'-cap, but additionally the modified RNA comprises at least one further modification as defined herein.

Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3' phosphorothioate, phosphorodithioate, or bridging or non-bridging methylphosphonate moiety. These modified 5'-cap structures are regarded as at least one modification comprised in the modified RNA according to the present invention.

Particularly preferred modified 5'-cap structures are CAP1 (methylation of the ribose of the adjacent nucleotide of m7G), CAP2 (methylation of the ribose of the $2^{nd}$ nucleotide downstream of the m7G), CAP3 (methylation of the ribose of the $3^{rd}$ nucleotide downstream of the m7G), CAP4 (methylation of the ribose of the $4^{th}$ nucleotide downstream of the m7G), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

Sequence Modification of the Open Reading Frame:

Modification of the G/C Content:

In a particularly preferred embodiment of the present invention, the G/C content of the coding region, encoding at least one peptide or protein of the modified RNA as defined herein, is modified, particularly increased, compared to the G/C content of its particular wild type coding region, i.e. the unmodified coding region. The encoded amino acid sequence of the coding region is preferably not modified compared to the coded amino acid sequence of the particular wild type coding region.

The modification of the G/C-content of the coding region of the modified RNA as defined herein is based on the fact that the sequence of any mRNA region to be translated is important for efficient translation of that mRNA. Thus, the composition and the sequence of various nucleotides are important. In particular, mRNA sequences having an increased G (guanosine)/C (cytosine) content are more stable than mRNA sequences having an increased A (adenosine)/U (uracil) content. According to the invention, the codons of the coding region are therefore varied compared to its wild type coding region, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage).

Depending on the amino acid to be encoded by the coding region of the modified RNA as defined herein, there are various possibilities for modification of the RNA sequence, e.g. the coding region, compared to its wild type coding region. In the case of amino acids, which are encoded by codons, which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present.

In contrast, codons which contain A and/or U nucleotides can be modified by substitution of other codons which code for the same amino acids but contain no A and/or U. Examples of these are:

the codons for Pro can be modified from CCU or CCA to CCC or CCG;

the codons for Arg can be modified from CGU or CGA or AGA or AGG to CGC or CGG;

the codons for Ala can be modified from GCU or GCA to GCC or GCG;

the codons for Gly can be modified from GGU or GGA to GGC or GGG.

In other cases, although A or U nucleotides cannot be eliminated from the codons, it is however possible to decrease the A and U content by using codons, which contain a lower content of A and/or U nucleotides. Examples of these are:

the codons for Phe can be modified from UUU to UUC;

the codons for Leu can be modified from UUA, UUG, CUU or CUA to CUC or CUG;

the codons for Ser can be modified from UCU or UCA or AGU to UCC, UCG or AGC;

the codon for Tyr can be modified from UAU to UAC;

the codon for Cys can be modified from UGU to UGC;

the codon for His can be modified from CAU to CAC;

the codon for Gln can be modified from CAA to CAG;

the codons for Ile can be modified from AUU or AUA to AUC;

the codons for Thr can be modified from ACU or ACA to ACC or ACG;

the codon for Asn can be modified from AAU to AAC;

the codon for Lys can be modified from AAA to AAG;

the codons for Val can be modified from GUU or GUA to GUC or GUG;

the codon for Asp can be modified from GAU to GAC;

the codon for Glu can be modified from GAA to GAG;

the stop codon UAA can be modified to UAG or UGA.

In the case of the codons for Met (AUG) and Trp (UGG), on the other hand, there is no possibility of sequence modification.

The substitutions listed above can be used either individually or in any possible combination to increase the G/C content of the coding region of the modified RNA as defined herein, compared to its particular wild type coding region (i.e. the original sequence). Thus, for example, all codons for Thr occurring in the wild type sequence can be modified to ACC (or ACG).

Preferably, the G/C content of the coding region of the modified RNA as defined herein is increased by at least 7%, more preferably by at least 15%, particularly preferably by at least 20%, compared to the G/C content of the wild type coding region. According to a specific embodiment at least 5%, 10%, 20%, 30%, 40%, 50%, 60%, more preferably at least 70%, even more preferably at least 80% and most preferably at least 90%, 95% or even 100% of the substitutable codons in the coding region encoding at least one peptide or protein, which comprises a pathogenic antigen or a fragment, variant or derivative thereof, are substituted, thereby increasing the G/C content of said coding region.

In this context, it is particularly preferable to increase the G/C content of the coding region of the modified RNA as defined herein, to the maximum (i.e. 100% of the substitutable codons), compared to the wild type coding region.

Codon Optimization:

According to the invention, a further preferred modification of the coding region encoding at least one peptide or protein of the modified RNA as defined herein, is based on the finding that the translation efficiency is also determined by a different frequency in the occurrence of tRNAs in cells. Thus, if so-called "rare codons" are present in the coding region of the wild type RNA sequence, to an increased extent, the mRNA is translated to a significantly poorer degree than in the case where codons coding for relatively "frequent" tRNAs are present.

In this context, the coding region of the modified RNA is preferably modified compared to the corresponding wild type coding region such that at least one codon of the wild type sequence, which codes for a tRNA which is relatively rare in the cell, is exchanged for a codon, which codes for a tRNA which is relatively frequent in the cell and carries the same amino acid as the relatively rare tRNA. By this modification, the coding region of the modified RNA as defined herein, is modified such that codons, for which frequently occurring tRNAs are available, are inserted. In other words, according to the invention, by this modification all codons of the wild type coding region, which code for a tRNA which is relatively rare in the cell, can in each case be exchanged for a codon, which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content, which is increased, in particular maximized, in the coding region of the modified RNA as defined herein, with the "frequent" codons without modifying the amino acid sequence of the peptide or protein encoded by the coding region of the RNA sequence. This preferred embodiment allows provision of a particularly efficiently translated and stabilized (modified) RNA sequence as defined herein.

In one embodiment, the RNA molecule having a cleavage site for a catalytic nucleic acid molecule is produced by non-enzymatic chemical RNA synthesis (e.g. Marshall and Kaiser, 2004. Curr. Opin. Chem. Biol. 8(3):222-229). That method is preferably employed in the case of an RNA molecule having a length of about 100 nucleotides or less. In a particularly preferred embodiment, the RNA molecule having a cleavage site for a catalytic nucleic acid molecule is synthesized in an in vitro transcription reaction.

In particularly preferred embodiments, the RNA molecule having a cleavage site for the catalytic nucleic acid molecule is a long RNA molecule comprising at least 100, 150, 200 or more preferably at least 500 nucleotides in length. Preferably, the RNA molecule has a length of from 5 to 30000 nucleotides, 10 to 25000 nucleotides, 50 to 20000 nucleotides, 100 to 18000 nucleotides, 300 to 15000 nucleotides or 500 to 12000 nucleotides.

The RNA molecule, which is analyzed by the method according to the invention, comprises a cleavage site for a catalytic nucleic acid molecule. Typically, the RNA molecule is cleaved at the cleavage site by the catalytic nucleic acid molecule, which yields a 5' terminal RNA fragment and at least one 3' RNA fragment. In general, the RNA molecule to be analyzed may comprise a cleavage site for any catalytic nucleic acid molecule, wherein the method is not limited with respect to a certain catalytic nucleic acid molecule. Typically, the cleavage site is specifically recognized by the respective catalytic nucleic acid molecule, preferably as defined herein, which is employed in the method according to the invention. As used herein, the cleavage site for the catalytic nucleic acid molecule may be comprised in the RNA molecule, e.g. because it is part of a naturally occurring coding sequence or a naturally occurring 5' UTR comprised in the RNA molecule. Preferably, the sequence of the RNA molecule has been designed or artificially modified in order to comprise a cleavage site for a catalytic nucleic acid molecule. Methods for changing or introducing nucleotides into DNA molecules to produce specific sites are known in the art. That DNA template can then be used to produce an RNA molecule, e.g. by in vitro transcription. These methods are known in the art. Preferably, the RNA molecule to be analyzed comprises a sequence, which is at least 30%, 40%, 50%, 60%, 70%, 80%, 90% or 95% identical to the consensus sequence of a cleavage site for a particular catalytic nucleic acid molecule.

For example, hairpin ribozymes cleave 5' of the guanosine in NGUC sequences, wherein N is any nucleotide. Furthermore, for example, a hammerhead ribozyme can be directed to cleave 3' of any NUH sequence, wherein N is any nucleotide, U is conserved, and H can be any nucleotide except G (N=G,A,C,U; H=A,C,U) (Haseloff and Gerlach, 1988. Nature 334: 585-591; McCall et al., 2000. Molecular Biotechnology 14: 5-17).

The RNA molecule to be analyzed comprises at least one cleavage site for the catalytic nucleic acid molecule. The RNA molecule may comprise any number of cleavage sites for the catalytic nucleic acid molecule, wherein the location of the most 5' cleavage site (i.e. the cleavage site, which is located closest to the 5' terminus of the RNA molecule) is preferably selected in order to allow separation and detection of the resulting 5' terminal RNA fragment.

Preferably, the location of the most 5' cleavage site is chosen such that cleavage of the RNA molecule at that site generates a 5' terminal RNA fragment that has a suitable size (i.e. number of nucleotides) in order to be separated by methods known in the art. Preferably, the most 5' cleavage site is located in a position between nucleotide positions 1 to 500 in 5'-3' direction of the RNA molecule, so that the resulting 5' RNA fragment has a size equal to or smaller than 500 nucleotides. More preferably, the most 5'cleavage site is located between nucleotide positions 1 and 400, 1 and 300, 1 and 200, 1 and 100 or 1 and 50 in 5'-3' direction of the RNA molecule, wherein "position 1" corresponds the 5' terminal nucleotide of the RNA molecule, "position 2" corresponds to the second nucleotide starting from the 5' terminus, and so forth. Most preferably, the cleavage site is located between nucleotide positions 1 and 5, 1 and 10, 1 and 20, 1 and 30, 1 and 40, 1 and 50, 1 and 60, 1 and 70, 1 and 80, 1 and 90 or 1 and 100 in 5'-3' direction of the RNA molecule. Even more preferably, the RNA molecule is cleaved by the catalytic nucleic acid molecule (in 5' to 3' direction) after nucleotide position 1, 2, 3, 4, 5, 6, 7, 8, 9, 10, 11, 12, 13, 14, 15, 16, 17, 18, 19, 20, 21, 22, 23, 24 or 25. In a particularly preferred embodiment, cleavage occurs between nucleotide position 5 and 15 or between position 8 and 20.

It is further preferred that the RNA molecule comprises an open reading frame encoding at least one protein or peptide, wherein the most 5' cleavage site for a catalytic nucleic acid molecule is located between the 5' terminus of the RNA molecule and the first nucleotide of the open reading frame. More preferably, the RNA molecule having a cleavage site is an mRNA molecule and comprises a 5'-UTR as defined herein. Preferably, the most 5' cleavage site is positioned in the 5'-UTR of said mRNA molecule.

Generally, the length of the 5' terminal RNA fragment resulting from the cleavage of the RNA molecule with a catalytic nucleic acid molecule is not limited in any way. In particular, according to the invention, the 5' terminal RNA fragment may have any length that allows separation and resolution of the fragment, preferably separation from a 3' RNA fragment. Depending, amongst other factors, on the physical property to be determined and depending on the means of separation that are envisaged, the skilled person may adapt the length of the 5' terminal RNA fragment by choosing the respective position of the most 5' cleavage site in the RNA molecule to be analyzed. Preferably, the most 5' terminal cleavage site in the RNA molecule is chosen such that cleavage with a catalytic nucleic acid molecule results in a 5' terminal RNA fragment, which comprises at least 1, 2, 3, 4, 5, 6, 7, 8, 9, 10, 11, 12, 13, 14, 15, 16, 17, 18, 19 or 20 nucleotides. Alternatively, the length of the 5' terminal RNA fragment is from 1 to 500, from 1 to 400, from 1 to 300, from 1 to 200, from 1 to 100, from 1 to 50 or from 1 to 30 nucleotides. In a particularly preferred embodiment, the location of the most 5' cleavage site in the RNA molecule is chosen such that the length of the 5' terminal RNA fragment resulting from the cleavage is from 5 to 20, from 8 to 25, from 10 to 20 or from 12 to 19 nucleotides.

The skilled person knows that one option to distinguish the 5' RNA fragments of interest from other nucleic acid molecules or fragments may be the choice of an appropriate size of the 5' RNA fragments by choosing an appropriate cleavage site, in particular by choosing an appropriate most 5' cleavage site. Alternatively, the 5' terminal RNA fragments are labelled with an appropriate marker so that the 5' terminal RNA fragments may be detected and distinguished from non-labelled fragments, e.g. 3' RNA fragments.

As used herein, the term "labelled" refers to an RNA molecule that is either directly or indirectly labelled with a molecule, which provides a detectable signal, e.g. radioisotope, fluorescent tag, chemiluminescent tag, a peptide or specific binding molecules. Specific binding molecules include pairs, such as biotin and streptavidin, digoxin and antidigoxin. The label can directly or indirectly provide a detectable signal. Radioisotopes (e.g. $^{18}F$, $^{125}I$, $^{35}S$, $^{14}C$, $^{3}H$, or $^{99m}Tc$) are commonly used in biological applications for the detection of a variety of nucleic acids such as RNA. Methods for the synthesis and labelling of RNA in vitro are known in the art (e.g. Huang and Yu, 2013. Synthesis and Labelling of RNA In Vitro. Current Protocols in Molecular Biology. 102:4.15.1-4.15.14).

For example, the synthesis and use of biotin labeled cap analogs has been described (Jemielity et al., 2012. Org. Biomol. Chem. 10(43):8570-4; WO2013/059475). These cap analogs can be incorporated into RNA molecules to produce 5'-capped and biotinylated RNAs, which retain their biological functionality and can be used for biotin-streptavidin technologies.

In a preferred embodiment, the method according to the invention uses a catalytic nucleic acid molecule that has been designed to be able to cleave the RNA molecule at a specific cleavage site, preferably at the most 5' cleavage site as described herein. Methods for designing catalytic nucleic acid molecules, in particular ribozymes that cleave RNA substrate molecules at a defined site, are known in the art.

For example, hairpin ribozymes cleave 5' of the guanosine in NGUC sequences, wherein N is any nucleotide. Furthermore, for example, a hammerhead ribozyme can be directed to cleave 3' of any NUH sequence, wherein N is any nucleotide, U is conserved, and H can be any nucleotide except G (N=G,A,C,U; H=A,C,U) (Haseloff and Gerlach, 1988. Nature 334: 585-591; McCall et al., 2000. Molecular Biotechnology 14: 5-17).

According to the substrate requirements of a catalytic nucleic acid molecule described above, an RNA molecule can—in principle—be expected to contain a number of possible sites for sequence-specific cleavage by a catalytic nucleic acid molecule. In addition to the target site, the number of base pairs to be formed between the catalytic nucleic acid molecule and the substrate are preferably chosen (substrate binding region). The affinity of a catalytic nucleic acid molecule towards its substrate can be adjusted by altering the length of the substrate binding region of the catalytic nucleic acid molecule. Although high affinity is usually desirable, an extended substrate binding region may cause problems regarding specificity and catalytic activity. Multiple turnover catalysis may be severely impaired if product release is slow due to strong binding of the target nucleic acid molecule to the catalytic nucleic acid molecule. Catalytic nucleic acid molecules with short binding arms (substrate binding region), however, may lack specificity.

Therefore, catalytic activity on the one hand and specificity on the other hand are preferably balanced when designing a catalytic nucleic acid molecule. Catalytic nucleic acid molecules, which form a larger number of base pairs with the substrate RNA, are less likely to dissociate from the cleaved substrate, and are thus not available for further cleavage. Therefore, the number of base pairs is preferably selected in such a way that the catalytic nucleic acid molecule-substrate complex formed is relatively stable under the conditions allowing the cleavage of the RNA molecule, but is able to dissociate once cleavage of the substrate has occurred. This typically requires 11 to 17 base pairs. Depending on the actual requirements in the specific case, that number may vary considerably. As a general rule, for specificity, the number of base pairs formed between the catalytic nucleic acid molecule and the substrate RNA should be high enough to make the target sequence unique, but not so high that imperfectly matched substrates would form stable complexes. Statistically, about 13 nucleotides are required to uniquely define a particular site in an RNA pool.

Methods for the production of catalytic nucleic acid molecules are known in the art. For example, a ribozyme can be chemically synthesized using the standard procedure for RNA synthesis as described (Wincott et al., 1995. Nucleic Acids Res. 23(14):2677-84). Ribozymes can also be synthesized by in vitro transcription of suitable DNA templates using e.g. bacteriophage T7 RNA polymerase (Haseloff and Gerlach, 1988. Nature 334: 585-591).

In this context, it is particularly preferred that the catalytic nucleic acid molecule is provided in trans. This means that the RNA molecule having a cleavage site for the catalytic nucleic acid molecule and the catalytic nucleic acid molecule are not part of the same molecule. However, the present invention also comprises the use of the catalytic nucleic acid molecule in cis, i.e. a situation, where the RNA molecule having a cleavage site and the catalytic nucleic acid molecule are part of the same molecule.

In a particularly preferred embodiment of the present invention, the catalytic nucleic acid molecule is a ribozyme. In this context it is particularly preferred that the ribozyme is selected from the group consisting of hammerhead ribozymes, hairpin ribozymes, and HDV ribozymes. In an even more preferred embodiment, the ribozyme is a hammerhead ribozyme.

Particularly preferred in this context is a hammerhead ribozyme comprising an RNA sequence according to SEQ ID NO: 1. Most preferably, the ribozyme comprising an RNA sequence according to SEQ ID NO: 1 specifically cleaves an RNA molecule 3' of the sequence motif NUH as shown in FIG. 5, wherein N is G, A, C, or U, and H is A, C, or U (Haseloff and Gerlach, 1988. Nature 334: 585-591; McCall et al., 2000. Molecular Biotechnology, 14: 5-17).

In an even more preferred embodiment a hammerhead ribozyme HHNUH2d according to SEQ ID NO: 2 is used in the method according to the invention. The ribozyme according to SEQ ID NO:2 specifically targets the 5' region of the RNA sequences according to SEQ ID NO: 3-5 and shown in FIGS. 1 to 3, forming helix III with mRNA positions 1-12, and helix I with mRNA positions 14-18 (FIG. 6) of the RNA sequences according to SEQ ID No: 3-5. The 5' region of the target RNA sequence contains two possible recognition sites, NUH1 (positions 10-12) and NUH2 (positions 11-13), of which NUH2 is the preferred target site.

```
Sequence of the trans-acting hammerhead ribozyme
HEINUH2d (SEQ ID NO: 2):
5'-GCAUGGCUGAUGAGGCCUCGACCGAUAGGUCGAGGCCGAAAAGCUUU
CUCCC-3'
```

In another particularly preferred embodiment, the catalytic nucleic acid molecule is a DNAzyme, e.g. a "10-23" DNAzyme.

By the cleavage with the catalytic nucleic acid molecule, the RNA molecule having at least one cleavage site for the catalytic nucleic acid molecule is specifically cleaved at that (at least one) defined site so that a 5' terminal and at least one 3' RNA fragment is produced.

Step b) of the methods as defined above comprises cleavage of the RNA molecule having a cleavage site for the catalytic nucleic acid molecule with the catalytic nucleic acid molecule. Therein, the RNA molecule is contacted with the catalytic nucleic acid molecule under conditions allowing the cleavage of the RNA molecule. Preferably, such conditions allow the specific interaction of the catalytic nucleic acid molecule and the RNA molecule having a cleavage site for the catalytic nucleic acid molecule, and the cleavage of the RNA molecule having a cleavage site. Such conditions may vary depending on the RNA molecule to be analyzed and the catalytic nucleic acid molecule that is employed. Nevertheless, methods are known in the art to select suitable conditions once a selection has been made concerning the RNA molecule to be analyzed and/or the catalytic nucleic acid molecule. The skilled person knows how to adjust the parameters, such as magnesium ion concentration, buffer composition, pH, temperature and incubation times.

Preferably, step b) of the method according to the invention comprises denaturing the nucleic acid molecules, preferably by heating, annealing the RNA molecule to be analyzed and the catalytic nucleic acid molecule and cleavage of the RNA molecule to be analyzed, wherein the annealing and the cleavage preferably take place at a lower temperature than the denaturing. Typically, the nucleic acid molecules (i.e. the RNA to be analyzed and the catalytic nucleic acid molecule) are heated either together (i.e. in a mixture) or separately in a suitable buffer that does preferably not contain magnesium ions ($Mg^{++}$). Subsequently, the nucleic acid molecules are cooled to cleavage reaction temperature, either together or separately. Preferably, the heating step involves heating of the buffer containing the nucleic acid molecules to a temperature of at least 70° C., more preferably at least 80° C., 85° C., 90° C., 95° C. or at least 96° C., preferably for at least 30 seconds, 60 seconds, 90 seconds or at least 120 seconds. After the heating step, the nucleic acid molecules are typically cooled down to the cleavage reaction temperature, which is typically lower than the temperature in the initial heating step. Preferably, the nucleic acid molecules are cooled in a controlled manner, for instance at a rate of 0.1° C. per second. The cleavage reaction preferably takes place at a temperature from 20° C. to 50° C., more preferably from 20° C. to 40° C., 24° C. to 38° C. or 25° C. to 37° C., most preferably at 25° C. or 37° C., for a period of preferably at least 1, 2, 3, 4, 5, 6, 7, 8, 9, 10, 15, 30, or 60 minutes. After cooling of the heated nucleic acid molecules and before starting the cleavage reaction (e.g. by addition of magnesium ions ($Mg^{++}$)), an optional annealing step is employed, wherein the temperature is preferably equal to the cleavage reaction temperature and which is typically carried out in absence of magnesium ions, preferably for at least 1, 2, 3, 4, 5, 6, 7, 8, 9 or at least 10 minutes.

Preferably, the RNA molecule to be analyzed and the catalytic nucleic acid molecule, preferably a ribozyme, are provided in about the same molar amounts.

In one embodiment, the catalytic nucleic acid molecule, preferably a ribozyme, and the RNA molecule to be analyzed are heated together at, for example, 95° C., preferably for 1 to 2 minutes, in the presence of buffer without magnesium ions, and subsequently cooled, preferably at a controlled cooling rate, to the reaction temperature of 20-37° C., preferably 25° C., in order to promote annealing. Subsequently, $Mg^{++}$ (e.g. $MgCl_2$) is added to initiate the cleavage reaction. In another embodiment, the catalytic nucleic acid molecule, preferably an ribozyme, and the RNA molecule to be analyzed are heated separately at, for example, 95° C. without $Mg^{++}$, preferably for one to two minutes, and are then cooled to the reaction temperature. $Mg^{++}$ is added to both the catalytic nucleic acid molecule and the RNA to be analyzed and the cleavage reaction is started by mixing both. In a preferred embodiment of the method according to the invention, the cleaving in step b) takes place in the presence of at least 10, 20 or 30 mM $Mg^{++}$, most preferably in presence of 30 mM $MgCl_2$.

In order to achieve a sufficient degree of cleavage of the RNA molecule to be analyzed, the $Mg^{++}$ concentration, buffer composition, pH value, temperature and reaction time may need to be adjusted. As used herein, the phrase "conditions allowing the cleavage of the RNA molecule" refers to conditions, which—at suitable incubation time—preferably allow cleavage of at least 50%, preferably at least 75%, 80%, 85%, 90%, 95% or 98% of the RNA molecules in a population, which have a cleavage site for a catalytic nucleic acid molecule. For example, "conditions allowing the cleavage of the RNA molecule" may comprise 50-200 mM NaCl or KCl, 0.1-200 mM $Mg^{++}$, 5-100 mM Tris-HCl, pH 6.5-8.5, 20-37° C. for 5 minutes to 2 hours. A non-ionic detergent (Tween, NP-40, Triton-X 100) is preferably present, usually at about 0.001 to 2%, typically 0.05-0.2% (volume/volume).

The cleavage of the RNA molecule having at least one cleavage site for a catalytic nucleic acid molecule with the catalytic nucleic acid molecule, leads to the generation of a 5' terminal RNA fragment and at least one 3' RNA fragment. The number of 3' RNA fragments depends on the number of cleavage sites for the catalytic nucleic acid molecule. For example, cleavage of an RNA molecule having one cleavage site typically leads to a 5' terminal RNA fragment and one 3' RNA fragment. On the other hand, cleavage of an RNA molecule having two cleavage sites typically results in three RNA fragments, i.e. a 5' terminal RNA fragments and two 3' RNA fragments.

Preferably, the 5' terminal RNA fragment obtained after cleavage of the RNA molecule to be analyzed with the catalytic nucleic acid molecule preferably comprises at least 1, 2, 3, 4, 5, 6, 7, 8, 9, 10, 11, 12, 13, 14, 15, 16, 17, 18, 19 or 20 nucleotides. Alternatively, the length of the 5' terminal RNA fragment is from 1 to 500, from 1 to 400, from 1 to 300, from 1 to 200, from 1 to 100, from 1 to 50 or from 1 to 30 nucleotides. In a particularly preferred embodiment, the length of the 5' terminal RNA fragment resulting from the cleavage of the RNA molecule having a cleavage site is from 5 to 20, from 8 to 25, from 10 to 20 or from 12 to 19 nucleotides.

Step c) of the method according to the invention comprises determining a physical property of the RNA molecule by analyzing the 5' terminal RNA fragment.

In the context of the present invention, the expression "a physical property" (or "physical properties") typically refers to a physical property or to a structural feature of an RNA molecule, preferably a modified RNA molecule as defined herein. Where the plural ("physical properties") is used, it may likewise refer to a single property or single feature. Preferably, the expression as used herein refers to a physical property or a structural feature of the RNA molecule, which distinguishes the RNA molecule from other, preferably structurally related, RNA molecules. Preferably, a physical property or a structural feature is capable of distinguishing the RNA molecule from a similar, preferably structurally related, RNA molecule lacking the physical property or a structural feature, more preferably from an RNA molecule, which is identical apart from the lacking physical property or the lacking structural feature. Typically, the distinct physical property reflects a structural feature, such as e.g. a distinct molecular weight, charge, or specific nucleotide composition. As used herein, a physical property or a structural feature may preferably be determined by standard analytical methods known in the art. Preferably, a physical property or a structural feature can be determined after cleavage of the RNA molecule having a cleavage site for a catalytic nucleic acid molecule. According to the invention, a distinct physical property or a distinct structural feature of the RNA molecule having a cleavage site for a catalytic nucleic acid molecule is determined by analysis of the 5' terminal RNA fragment obtained after cleavage of the RNA molecule with the catalytic nucleic acid molecule. In other words, the 5' terminal RNA fragment obtained by cleavage of the RNA molecule having a cleavage site for a catalytic nucleic acid molecule with the catalytic nucleic acid molecule reflects a physical property or a structural feature of the RNA molecule. Thus, by analyzing the 5' terminal RNA fragment, preferably with respect to a distinct physical property or a structural feature as defined herein, a distinct physical property of the RNA molecule, from which the 5' terminal RNA fragment is derived, is determined. In a preferred embodiment, the physical property or structural feature is selected from the molecular weight, the charge, the nucleotide sequence, and the presence or absence, respectively, of a nucleotide, preferably a modified nucleotide, a 5' terminal modification as defined herein, or a specific moiety of a nucleotide, preferably of a modified nucleotide, such as a modified base, in the 5' terminal RNA fragment.

In a preferred embodiment, step c) involves separating or resolving the 5' terminal RNA fragment from the at least one 3' RNA fragment. In order to determine the physical property of the 5' terminal RNA fragment—or the respective RNA molecule, from which it is derived—it is typically sufficient to resolve the fragment in any manner, i.e. to employ an analytic technique that allows to determine the presence or absence of an RNA fragment with certain physical properties. By determining the presence or absence of said fragment with a certain physical property, the skilled person is capable of determining the physical property of the RNA molecule, from which the fragment is derived. To this end, the fragment does not necessarily need to be physically separated or isolated from another fragment or other fragments that may be present. The resolution of a fragment with a certain physical property may also be achieved in mixture, e.g. by using labelling techniques or molecular markers and relevant methods for detection.

In one embodiment, the 5' terminal RNA fragment is separated from another fragment, preferably from the at least one 3' RNA fragment. Any suitable method for separating RNA fragments can be used, including, but not limited to, denaturing gel electrophoresis or liquid chromatography. In general, the separation technique is used according to the characteristics, e.g. the size, of the fragments to be separated. The skilled person can thus select a suitable separation technology on the basis of the characteristics of the expected fragment.

In a particularly preferred embodiment of the first aspect of the present invention, the RNA fragments are separated in step c) by denaturing gel electrophoresis or liquid chromatography, preferably HPLC, FPLC or RPLC. Separation of RNA molecules by denaturing gel electrophoresis has been described (Maniatis et al., 1975. Biochemistry 14(17):3787-3794). For example, polyacrylamide gels that contain a high concentration of a denaturing agent such as urea are capable of resolving short (<500 nucleotides) single-stranded RNA fragments that differ in length by as little as one nucleotide. In this context, polyacrylamide gels comprising urea, preferably 8 M urea, are particularly preferred.

The RNA fragments obtained by cleavage of the RNA molecule having a cleavage site for a catalytic nucleic acid molecule can also be separated by liquid chromatography. As used herein, the term "liquid chromatography" (LC) preferably refers to a process of selective retardation of one or more components of a fluid solution as the fluid uniformly percolates through a column of a finely divided, preferably porous, substance, or through capillary passageways. The retardation results from the distribution of the components of the mixture between one or more stationary phases and the bulk fluid (i.e. the mobile phase), as this fluid moves relative to the stationary phase(s). LC includes reverse phase liquid chromatography (RPLC), high performance liquid chromatography (HPLC), high turbulence liquid chromatography (HTLC) and fast performance liquid chromatography (FPLC). In contrast to HPLC, the buffer pressure used in FPLC is relatively low, typically less than 5 bar, but the flow rate is relatively high, typically 1-5 ml/min.

Stationary phases for the use in liquid chromatography are known in the art. Preferably, the stationary phase is selected from the group consisting of a porous polystyrene, a porous non-alkylated polystyrene, a polystyrenedi-vinylbenzene, a porous non-alkylated polystyrenedivinylbenzene, a porous silica gel, a porous silica gel modified with non-polar residues, a porous silica gel modified with alkyl containing residues, selected from butyl-, octyl and/or octadecyl containing residues, a porous silica gel modified with phenylic residues, and a porous polymethacrylate (see also WO2008077592, the disclosure of which is incorporated herewith by reference).

In this context, ethylene-bridged hybrid organic/inorganic stationary phases are particularly preferred (see also Wyndham et al., 2003. Anal. Chem. 75(24):6781-8 and WO2003014450, the disclosure of which is incorporated herewith by reference).

For example, the separation process of RNA molecules by HPLC has been described (Weissman et al., 2013. Methods Mol. Biol. 969:43-54).

In a preferred embodiment, the separation of the 5' terminal RNA fragment in itself already reveals the distinct property of the RNA molecule, from which it is derived and which is to be analyzed. For example, if the presence of an extra nucleotide or a modification at the 5' terminal RNA fragment is investigated, then it is typically enough to separate the fragments in order to obtain the result.

Preferably, step c) comprises comparison of a structural feature or of a physical parameter of the 5' terminal RNA fragment, and the respective feature or parameter of a reference RNA fragment. For example, a 5' terminal RNA fragment may be compared to a reference RNA fragment, which is known to exhibit a certain property, in order to confirm that property in the 5' terminal RNA fragment obtained in step b). Preferably, this comparison is carried out after separation of the 5' terminal RNA fragment obtained in step b).

In another preferred embodiment, the separated fragment is further analyzed by further analytical methods in order to determine the distinct physical property of the fragment.

In a preferred embodiment, the physical property of the 5' terminal RNA fragment is determined in step c) by spectroscopic methods, quantitative mass spectrometry, or sequencing.

Spectroscopic methods for RNA analysis include traditional absorbance measurements at 260 nm and more sensitive fluorescence techniques using fluorescent dyes such as ethidium bromide and a fluorometer with an excitation wavelength of 302 or 546 nm (Gallagher, 2011. Quantitation of DNA and RNA with Absorption and Fluorescence Spectroscopy. Current Protocols in Molecular Biology. 93:A.3D.1-A.3D.14).

A mass spectrometer (MS) is a gas phase spectrometer that measures a parameter that can be translated into mass-to-charge ratio of gas phase ions. Examples of mass spectrometers are time-of-flight, magnetic sector, quadrupole filter, ion trap, ion cyclotron resonance, electrostatic sector analyser and hybrids of these. Methods for the application of MS methods to the characterization of nucleic acids are known in the art.

For example, Matrix-Assisted Laser Desorption/Ionization Mass Spectrometry (MALDI-MS) can be used to analyse oligonucleotides at the 120-mer level and below (Castleberry et al., 2008. Matrix-Assisted Laser Desorption/Ionization Time-of-Flight Mass Spectrometry of Oligonucleotides. Current Protocols in Nucleic Acid Chemistry. 33:10.1.1-10.1.21).

Electrospray Ionization Mass Spectrometry (ESI-MS) allows the analysis of high-molecular-weight compounds through the generation of multiply charged ions in the gas phase and can be applied to molecular weight determination, sequencing and analysis of oligonucleotide mixtures (Castleberry et al., 2008. Electrospray Ionization Mass Spectrometry of Oligonucleotides. Current Protocols in Nucleic Acid Chemistry. 35:10.2.1-10.2.19). Preferably, the mass spectrometry analysis is conducted in a quantitative manner to determine the amount of RNA.

Methods for sequencing of RNA are known in the art. A recently developed technique called RNA Sequencing (RNA-Seq) uses massively parallel sequencing to allow for example transcriptome analyses of genomes at a far higher resolution than is available with Sanger sequencing- and microarray-based methods. In the RNA-Seq method, complementary DNAs (cDNAs) generated from the RNA of interest are directly sequenced using next-generation sequencing technologies. RNA-Seq has been used successfully to precisely quantify transcript levels, confirm or revise previously annotated 5' and 3' ends of genes, and map exon/intron boundaries (Eminaga et al., 2013. Quantification of microRNA Expression with Next-Generation Sequencing. Current Protocols in Molecular Biology. 103:4.17.1-4.17.14). Consequently, the amount of the RNA fragments can be determined also by RNA sequencing.

In a preferred embodiment, step c) comprises analyzing the 5' terminal RNA fragment by comparison to a reference fragment. In particular, step c) comprises comparison of a structural feature or of a physical parameter of the 5' terminal RNA fragment and the respective feature or parameter of a reference RNA fragment. Preferably, at least one reference 5' terminal RNA fragment is used as reference. The 5' terminal RNA fragment obtained in step b) of the method according to the invention is thus compared to one or more reference fragments. For example, a 5' terminal fragment having a physical property of interest (e.g. the presence of a certain modification, such as a 5' cap structure) may be analyzed in parallel with the 5' terminal RNA fragment derived from an RNA molecule, which is to be analyzed.

In a preferred embodiment, the method according to the invention is used for controlling the quality of RNA, preferably for controlling the quality of in vitro produced RNA. Preferably, the method is employed for controlling the quality of artificial RNA, preferably an mRNA, which is preferably synthesized by in vitro transcription.

According to one embodiment, the method is used for determining a structural feature in an RNA molecule, preferably a modified RNA molecule, having a cleavage site for a catalytic nucleic acid molecule, wherein the structural feature is located between the 5' terminus of the RNA molecule and the cleavage site for a catalytic nucleic acid molecule. In one embodiment, the method is used for determining the presence of a 5' terminal modification as defined herein. Preferably, the method is used for determining a structural feature selected from the presence or absence of a cap structure, the orientation of a cap structure, the presence of a modified cap structure, e.g. a cap analog as described herein, or any other modification, such as a base modification.

In a particularly preferred embodiment, step c) of the method according to the invention comprises determining the presence or the absence of a cap structure at the 5' terminus of the RNA molecule having a cleavage site for the catalytic nucleic acid molecule, wherein the RNA molecule preferably comprises at least one modification. The 5' terminal RNA fragment of a capped RNA differs from the 5' terminal RNA fragment of an uncapped RNA—which is otherwise identical—by one nucleotide, i.e. the 5' cap structure. That distinct property is exploited in order to determine the capping status of the RNA molecule to be analyzed by analyzing the 5' terminal RNA fragment.

In this context, the RNA molecule, preferably an mRNA molecule, having a cleavage site for the catalytic nucleic acid molecule may be produced by in vitro transcription in the presence of a cap analog (co-transcriptional capping). Capped in vitro transcripts can be synthesized by substituting a cap analog such as a m7G(5')ppp(5')G (m7G) for a portion of the GTP in the transcription reaction, typically the cap analog is used at a four-fold excess compared to GTP. Methods for in vitro transcription are known in the art (Geall et al., 2013. Semin. Immunol. 25(2): 152-159) and typically include:

1) a linearized DNA template with a promoter sequence that has a high binding affinity for its respective RNA polymerase such as bacteriophage-encoded RNA polymerases, 2) ribonucleotide triphosphates (NTPs) for the four bases (adenine, cytosine, guanine and uracil);

3) a cap analog as defined above (e.g. m7G(5')ppp(5')G (m7G));

4) a DNA-dependent RNA polymerase (e.g. T7, T3 or SP6 RNA polymerase);

5) a ribonuclease (RNase) inhibitor to inactivate any contaminating RNase;

6) a pyrophosphatase to degrade pyrophosphate, which may inhibit transcription;

7) $MgCl_2$, which supplies $Mg^{2+}$ as a co-factor for the polymerase;

8) a buffer to maintain a suitable pH value, which can also contain antioxidants and polyamines such as spermidine at optimal concentrations.

In a preferred embodiment, the cap analog is selected from the group consisting of G[5']ppp[5']G, m$^7$G[5']ppp[5']G, $m_3^{2,2,7}$G[5']ppp[5']G, $m_2^{7,3'-O}$G[5']ppp[5']G (3'-ARCA), $m_2^{7,2'-O}$GpppG (2'-ARCA), $m_2^{7,2'-O}$GppspG D1 (β-S-ARCA D1) and $m_2^{7,2'-O}$GppspG D2 (β-S-ARCA D2).

In another preferred embodiment, the RNA molecule, preferably the mRNA molecule, to be analyzed is produced by in vitro transcription and subsequent enzymatic capping (e.g. post-transcriptional capping). Vaccinia Virus Capping Enzyme (VCE) possesses all three enzymatic activities necessary to synthesize an m7G cap structure (RNA 5'-triphosphatase, guanylyltransferase, and guanine-7-methyltransferase). In vitro transcripts can be capped in the presence of the capping enzyme, reaction buffer, GTP, and the methyl donor S-adenosylmethionine (SAM). Using GTP as substrate the VCE reaction yields RNA caps in the correct orientation. In addition, a type 1 cap can be created by adding a second Vaccinia enzyme, 2' O methyltransferase, to the capping reaction. RNA carrying type I caps are reported to have enhanced translational activity compared to type 0 caps (Tcherepanova et al., 2008. BMC Mol. Biol. 9:90).

In a preferred embodiment, the cleavage site in the RNA molecule is chosen in such a way that the resulting 5' terminal RNA fragment can be separated or resolved, as described herein. Any size is possible for the 5' terminal RNA fragment, as long as the produced capped or non-capped 5' terminal RNA fragment, which typically differ in length by one nucleotide—can be identified. The skilled person will understand that one option to distinguish the 5' terminal RNA fragment from other nucleic acid molecules may be the selection of an appropriate size of the 5' terminal RNA fragment by choosing an appropriate cleavage site. Alternatively or in addition to the aforementioned, the 5' terminal RNA fragment may also be labeled, preferably as described herein, with an appropriate marker allowing specific detection of the 5' terminal RNA fragment. In addition or alternatively to the separation methods mentioned above, any suitable further analytical method, preferably as described herein, may be employed in order to determine whether the obtained 5' terminal RNA fragment is capped or not.

Preferably, a reference RNA fragment (i.e. a fragment sharing the same RNA sequence and having a known capping status) is analyzed in parallel to the 5' terminal RNA fragment, which is derived from the RNA molecule to be analyzed. For example, a capped reference fragment is used in parallel as a control in step c) of the method. The skilled person knows how to synthesize such fragments, e.g. chemically or by enzymatic capping of an RNA molecule.

In another embodiment, the method of the invention concerns a method, wherein the RNA molecule, preferably an mRNA molecule, more preferably a modified mRNA molecule, having a cleavage site for the catalytic nucleic acid molecule comprises a cap structure at the 5' terminus and step c) comprises determining the orientation of the cap.

As mentioned above, a capped RNA molecule may comprise a 5' terminal cap structure having, for example, the general structure mGpppG, wherein "mG" is the cap structure (modified guanine nucleotide, for instance, methylated at carbon 7), "ppp" is a 5' to 5' triphosphate linkage and "G" is a guanine nucleotide, wherein "G" represents position 1 of an RNA molecule as defined herein and is thus linked to position 2 of that RNA molecule. "G" is preferably non-methylated, whereas "mG" is preferably methylated, e.g. on carbon 7 and/or carbon 2. Thus, an RNA molecule having a 5' terminus comprising a structure such as "5'-mG-ppp-G-N-3'", wherein "N" is the nucleotide at position 2, as defined herein, of the RNA molecule, is referred to herein as "correctly capped" RNA molecule. On the other hand, a capped RNA molecule may—as an alternative—comprise a 5' terminal structure, such as "5'-G-ppp-Gm-N-3'", wherein the modified guanine Gm, e.g. a guanine nucleotide methylated at carbon 7, is positioned closer to the nucleotide at position 2 of the RNA molecule. Such an RNA molecule is referred to herein as "reverse-capped" RNA molecule.

For example, reverse-capped RNA molecules are synthesized—as a side product—by in vitro transcription, preferably by in vitro transcription, which is carried out in presence of a dinucleotide cap analog (such as m7G(5')ppp (5')G (m7G)), also known as co-transcriptional capping.

The orientation is preferably determined by using a suitable analytical method as described above. The 5' terminal RNA fragment of a correctly capped RNA molecule and the 5' terminal RNA fragment of a reverse-capped RNA molecule, wherein the only difference between the correctly capped and the reverse-capped RNA molecule is the orientation of the cap, typically have the same mass. Nevertheless, the distinct orientation is associated with a physical property that is determined by using the method according to the invention. For example, fragments having the same mass may interact in a distinct manner with the stationary and/or the mobile phase in a chromatography assay, thus allowing the resolution of two 5' terminal RNA fragments, which differ only by the orientation of the cap structure, by means of chromatography.

In a preferred embodiment, the invention provides a method for analyzing a capped RNA, preferably a capped modified RNA as defined herein, having a cleavage site for a catalytic nucleic acid molecule, wherein step c) comprises separating a 5' terminal RNA fragment from the at least one 3' RNA fragment, preferably by the means described herein, and determining the orientation of the 5' cap structure at the 5' terminus of the fragment. Preferably, the 5' terminal RNA fragment is separated by a chromatographic technique, preferably reversed-phase chromatography. In one embodiment, the fragment is analyzed in a HPLC system In a preferred embodiment, step c) comprises determining the orientation of a cap structure in a 5' terminal RNA fragment, which comprises comparison with a reference fragment. Preferably, a capped reference fragment is used, of which the capping orientation is known. More preferably, an enzymatically capped RNA is used for synthesizing the reference fragment.

In addition, it has been found that the method according to the invention is useful for characterizing a population of RNA molecules, preferably as defined herein. Preferably, the method is for analyzing a modified RNA molecule as defined herein. Specifically, the invention provides a method for analyzing a population of RNA molecules, wherein the population comprises at least one RNA molecule that has a cleavage site for a catalytic nucleic acid molecule, the method comprising the steps of:
  a) providing a sample containing the population of RNA molecules,
  b) cleaving the at least one RNA molecule having a cleavage site for the catalytic nucleic acid molecule with the catalytic nucleic acid molecule into a 5' terminal RNA fragment and at least one 3' RNA fragment by contacting the sample with the catalytic nucleic acid molecule under conditions allowing the cleavage of the RNA molecule,
  c) determining a physical property of the at least one RNA molecule having a cleavage site by analyzing the at least one 5' terminal RNA fragment obtained in step b), and
  d) measuring the relative amount of the at least one 5' terminal RNA fragment obtained in step b), thereby determining the relative amount of RNA molecules having said physical properties in the RNA population.

While steps a), b) and c) are typically as defined herein for the method for analyzing an RNA molecule having a cleavage site for a catalytic nucleic acid molecule, step d) of the method for analyzing a population of RNA molecules is specific for the latter. Hence, all the features described above for steps a), b) and c) applies in analogous manner to the method for analyzing an RNA population. The method for analyzing an RNA population, however, additionally comprises step d), which comprises measuring the relative amount of the at least one 5' terminal RNA fragment obtained in step b), thereby determining the relative amount of RNA molecules having said physical properties in the RNA population.

As used herein, the population of RNA molecules typically comprises at least one RNA molecule, preferably a modified RNA molecule, having a cleavage site for a catalytic nucleic acid molecule, wherein the at least one RNA molecule is characterized by a distinct physical property or a distinct structural feature, which may preferably be determined by analyzing the 5' terminal RNA fragment obtained in step b) of the method for analyzing the RNA population. Preferably, a population of RNA molecules comprises at least one first RNA molecule having a cleavage site for a catalytic nucleic acid molecule, and further comprises at least one second RNA molecule having a cleavage site for a catalytic nucleic acid molecule, wherein the first RNA molecule and the second RNA molecule differ in a physical property or a structural feature that may be determined by analyzing the respective 5' terminal RNA fragments. By measuring the relative amounts of those 5' terminal RNA fragments, the relative amounts of the respective RNA molecules in the population of RNA molecules are determined. Therein, the relative amounts of the 5' terminal RNA fragments are measured by using any suitable technique for nucleic acid molecule quantitation, preferably by using the techniques described herein. In a preferred embodiment, the amounts of the 5' terminal RNA fragments are measured in step c) by spectroscopic methods, quantitative mass spectrometry, or sequencing. Step d) preferably comprises calculating the ratio of the amount of an RNA molecule with a distinct physical property to the amount of another RNA molecule in the population or to the total amount of RNA molecules in the population.

In a preferred embodiment of the method for analyzing an RNA population, the population comprises at least one capped RNA molecule having a cleavage site for the catalytic nucleic acid molecule. Therein, step d) preferably comprises determining the relative amount of capped RNA molecules in the population, preferably by measuring the total amount of 5' terminal RNA fragments and the amount of capped 5' terminal RNA fragments.

Preferably, the population comprises at least one capped RNA molecule having a cleavage site for the catalytic nucleic acid molecule and at least one non-capped RNA molecule having a cleavage site for the catalytic nucleic acid molecule. In that embodiment, step c) comprises separating capped 5' terminal RNA fragments and non-capped 5' terminal RNA fragments. Preferably, the amounts of capped and non-capped 5' terminal RNA fragments are measured and step d) comprises calculating the ratio of the amount of capped RNA molecules having a cleavage site for the catalytic nucleic acid molecule and the amount of non-capped RNA molecules having a cleavage site for the catalytic nucleic acid molecule in the population. The relative amount (in percent) of capped RNA molecules with respect to the total amount of RNA molecules in the RNA population is also referred to herein as "capping degree".

In a preferred embodiment, the relative amounts (in percent) of capped and non-capped 5' terminal RNA fragments—or capped and non-capped RNA molecules to be analyzed—is calculated. In this context, reference is also made to Example 3.

$$\text{capped RNA}(\%) = \frac{\text{amount of capped RNA}}{\sum \text{amount(non-capped RNA + capped RNA)}} \times 100$$

$$\text{non-capped RNA}(\%) = \frac{\text{amount non-capped RNA}}{\sum \text{amount(non-capped RNA + capped RNA)}} \times 100$$

In another embodiment, the population comprises at least one correctly capped RNA molecule as defined herein having a cleavage site for the catalytic nucleic acid molecule and step d) comprises determining the relative amount of correctly capped RNA molecules having a cleavage site for the catalytic nucleic acid molecule in the population, preferably by measuring the total amount of 5' terminal RNA fragments and the amount of correctly capped 5' terminal RNA fragments.

Preferably, the population comprises at least one correctly capped RNA molecule having a cleavage site for the catalytic nucleic acid molecule and at least one reverse-capped RNA molecule having a cleavage site for the catalytic nucleic acid molecule. In that embodiment, step c) comprises separating correctly capped 5' terminal RNA fragments and reverse-capped 5' terminal RNA fragments. Preferably, the amounts of correctly capped and reverse-capped 5' terminal RNA fragments are measured and step d) comprises calculating the ratio of the amount of correctly capped RNA molecules having a cleavage site for the catalytic nucleic acid molecule and the amount of reverse-capped RNA molecules having a cleavage site for the catalytic nucleic acid molecule in the population.

In a particularly preferred embodiment, the method for analyzing an RNA population comprises both, determining the relative amount of capped RNA molecules in the RNA population and determining the relative amount of correctly capped RNA molecules. The population comprises at least one RNA molecule having a cleavage site for a catalytic nucleic acid molecule, wherein the RNA molecule is preferably modified as defined herein. The method is not limited as to which property is determined first. In a preferred embodiment, a technique is selected in step c) which allows both, determining the presence of a cap and determining the orientation of a cap structure. Preferably, step c) comprises a chromatography technique, more preferably a liquid chromatography technique as described herein or most preferably a HPLC technique. In a particularly preferred embodiment, step c) comprises a chromatography technique and a spectrometry technique, such as a mass spectrometry technique.

In a further aspect, the present invention relates to a method of determining the capping degree of a population of RNA molecules having a cleavage site for a catalytic nucleic acid molecule, comprising the steps of:
a) providing a sample containing the population of RNA molecules,
b) cleaving the RNA molecules with the catalytic nucleic acid molecule into a 5' terminal RNA fragment and at least one 3' RNA fragment by contacting the sample with the catalytic nucleic acid molecule under conditions allowing the cleavage of the RNA molecules,
c) separating the RNA fragments obtained in step b),
d) determining a measure for the amount of the capped and non-capped 5' terminal RNA fragments separated in step c) of said population of RNA molecules, and
e) comparing said measures of capped and non-capped 5' terminal RNA fragments determined in step d), thereby determining the capping degree of said population of RNA molecules.

In the context of the present invention, it has been found that the method of the present invention is suitable for the determination of the capping degree of a population of RNA molecules. The method of the invention is especially suitable because it allows the characterization of the capping degree of a population of RNA molecules of any length, including very long RNA molecules. Very long RNA molecules comprise at least 1000 nucleotides in length. This is achieved by cleaving the RNA molecules with a catalytic nucleic acid molecule at a known site resulting in 5'-terminal RNA fragments of the RNA molecules which can be used to differentiate between capped and non-capped RNA molecules.

According to the invention, the term "capped RNA molecule" or "capped RNA fragment" means that the RNA molecule or the RNA fragment bears at its 5'-terminus a 5' cap structure as defined above.

The capped and non-capped RNA molecules or 5'-RNA fragments of the population only differ by one nucleotide in size, because typically the size of a 5' cap structure corresponds to the length of one nucleotide.

According to the invention, the term "capping degree" indicates how many of the RNA molecules of the population have a cap at their 5' end, in particular, this term indicates the percentage of capped RNA molecules of the population.

In particularly preferred embodiments the RNA molecules are long RNA molecules comprising at least 100, 150, 200 or more preferably at least 500 nucleotides in length.

Preferably the RNA molecules of the population used according to the invention comprise at least one open reading frame coding for at least one peptide or protein.

In this context the RNA molecules of the population can comprise one (monocistronic), two (bicistronic) or more (multicistronic) open reading frames (ORF). The RNA molecules of the population can be messenger RNA (mRNA) molecules, viral RNA molecules or self-replicating RNA molecules (replicons).

Preferably the RNA molecules of the population are mRNA molecules.

Preferably the RNA molecules of the population are primary microRNA (pri-miRNA) molecules.

It is known that miRNAs are first transcribed as a largely unstructured precursor, termed a primary miRNA (pri-miRNA), which is sequentially processed in the nucleus, to give the approximately 65-nt pre-miRNA hairpin intermediate, and then in the cytoplasm, to give the mature miRNA. These pre-miRNA molecules can be capped and polyadenylated (Cai et al., 2004. RNA 10(12):1957-66).

According to the invention, the RNA molecules of the population comprise a cleavage site for a catalytic nucleic acid molecule allowing the cleavage of the RNA molecules of the population into a 5' RNA fragment and at least one 3' RNA fragment. In a preferred embodiment, the cleavage site in the RNA molecule is chosen in such a way that short enough capped and non-capped 5' RNA fragments are produced that can be separated. In general, and as known by the person skilled in the art, the choice of the cleavage site (and thereby the length of the obtained RNA fragments) will also depend on the separation method used and its resolution capacity to discriminate between RNA fragments of different length. Since the capped 5' RNA fragment originating from a capped RNA molecule of the population is usually about only one nucleotide longer than the non-capped 5'

RNA fragment originating from a non-capped RNA molecule of the population, single-nucleotide resolution is necessary. Preferably, the defined cleavage site is located between nucleotide positions 1 to 500 in 5'-3' direction of the RNA molecule, so that the resulting 5' RNA fragment has a size equal to or smaller than 500 nucleotides. More preferred, the defined cleavage site is located between nucleotide positions 1 to 400, 1 to 300, 1 to 200 or 1 to 100 in 5'-3' direction of the RNA molecule. Most preferred, the defined cleavage site is located between nucleotide positions 1 to 5, 1 to 10, 1 to 20, 1 to 30, 1 to 40, 1 to 50, 1 to 60, 1 to 70, 1 to 80, 1 to 90 or 1 to 100 in 5'-3' direction of the RNA molecule.

Any of the above sizes are possible as long as the produced capped and non-capped 5' RNA fragments can be distinguished from each other, from the catalytic nucleic acid molecule, and from other nucleic acid molecules, especially from the 3' RNA fragments. The skilled person will understand that one option to distinguish the 5' RNA fragments of interest from other nucleic acid molecules may be the choice of an appropriate size of the 5' RNA fragments by choosing an appropriate cleavage site. Another option is to provide the 5' RNA fragments with an appropriate marker so that the 5' RNA fragments are labeled which allows the specific detection of the cleaved 5' RNA fragments.

By "labeled" is meant that the RNA molecule is either directly or indirectly labeled with a molecule which provides a detection signal, e.g. radioisotope, fluorescent tag, chemiluminescent tag, a peptide or specific binding molecules. Specific binding molecules include pairs, such as biotin and streptavidin, digoxin and antidigoxin. The label can directly or indirectly provide a detectable signal. Radioisotopes (e.g. $^{18}F$, $^{125}I$, $^{35}S$, $^{14}C$, $^{3}H$, or $^{99m}Tc$) are commonly used in biological applications for the detection of a variety of nucleic acids such as RNA. Methods for the synthesis and labelling of RNA in vitro are known in the art (e.g. Huang and Yu, 2013. Synthesis and Labelling of RNA In Vitro. Current Protocols in Molecular Biology. 102:4.15.1-4.15.14).

For example, the synthesis and use of biotin labeled cap analogs has been described (Jemielity et al., 2012. Org. Biomol. Chem. 10(43):8570-4; WO2013/059475). These cap analogs can be incorporated into RNA molecules to produce 5'-capped and biotinylated RNAs which retain their biological functionality and can be used for biotin-streptavidin technologies.

In the first step of the method according to the invention, a sample containing the population of RNA molecules is provided.

The method according to the present invention can be performed with any RNA preparation as a starting material, as long as the respective population of RNA molecules of interest is present in the preparation. The RNA preparation can be derived from a cell endogenously expressing said population of RNA molecules of interest or a cell that is transfected with a nucleic acid such as DNA or RNA or infected by a virus and therefore expressing said population of RNA molecules. For example, said RNA preparation can be derived from a cell, tissue, organ, organism, bacterial cell or virus. Methods for the isolation of RNA from these sources are known in the art (Liu and Harada, 2013. RNA Isolation from Mammalian Samples. Current Protocols in Molecular Biology. 103:4.16.1-4.16.16).

In the context of the present invention, the term "endogenously" means that the respective cell expresses said population of RNA molecules without being transfected with an RNA-encoding nucleic acid.

The sample containing the population of RNA molecules provided in the first step of the method according to the present invention may, apart from the population of RNA molecules of interest, also contain other nucleic acid molecules, especially other RNA molecules.

In a preferred embodiment of the first aspect of the present invention, the sample containing the population of RNA molecules is generated by in vitro transcription in the presence of a cap analog or by in vitro transcription and subsequent enzymatic capping.

In this context, the population of RNA molecules may be produced by in vitro transcription in the presence of a cap analog (co-transcriptional capping). Capped in vitro transcripts can be synthesized by substituting a cap analog such as a m7G(5')ppp(5')G (m7G) for a portion of the GTP in the transcription reaction, typically the cap analog is used at a four-fold excess compared to GTP. Methods for in vitro transcription are known in the art (Geall et al., 2013. Semin. Immunol. 25(2): 152-159) and typically include:

1) a linearized DNA template with a promoter sequence that has a high binding affinity for its respective RNA polymerase such as bacteriophage-encoded RNA polymerases, 2) ribonucleotide triphosphates (NTPs) for the four bases (adenine, cytosine, guanine and uracil);

3) a cap analog as defined above (e.g. m7G(5')ppp(5')G (m7G));

4) a DNA-dependent RNA polymerase (e.g. T7, T3 or SP6 RNA polymerase);

5) a ribonuclease (RNase) inhibitor to inactivate any contaminating RNase;

6) a pyrophosphatase to degrade pyrophosphate, which may inhibit transcription;

7) $MgCl_2$, which supplies $Mg^{2+}$ as a co-factor for the polymerase;

8) a buffer to maintain a suitable pH value, which can also contain antioxidants and polyamines such as spermidine at optimal concentrations.

In a preferred embodiment, the cap analog is selected from the group consisting of G[5']ppp[5']G, $m^7$G[5']ppp[5']G, $m_3^{2,2,7}$G[5']ppp[5']G, $m_2^{7,3'-O}$G[5']ppp[5']G (3'-ARCA), $m_2^{7,2'-O}$GpppG (2'-ARCA), $m_2^{7,2'-O}$GppspG D1 (β-S-ARCA D1) and $m_2^{7,2'-O}$GppspG D2 (β-S-ARCA D2).

In another preferred embodiment, the population of RNA molecules is produced by in vitro transcription and subsequent enzymatic capping (e.g. post-transcriptional capping). Vaccinia Virus Capping Enzyme (VCE) possesses all three enzymatic activities necessary to synthesize an m7G cap structure (RNA 5'-triphosphatase, guanylyltransferase, and guanine-7-methyltransferase). In vitro transcripts can be capped in the presence of the capping enzyme, reaction buffer, GTP, and the methyl donor S-adenosylmethionine (SAM). Using GTP as substrate the VCE reaction yields RNA caps in the correct orientation. In addition, a type 1 cap can be created by adding a second Vaccinia enzyme, 2' O methyltransferase, to the capping reaction. RNA carrying type I caps are reported to have enhanced translational activity compared to type 0 caps (Tcherepanova et al., 2008. BMC Mol. Biol. 9:90).

In a further preferred embodiment, the population of RNA molecules is produced by non-enzymatic chemical RNA synthesis (e.g. Marshall and Kaiser, 2004. Curr. Opin. Chem. Biol. 8(3):222-229). Currently, the length of RNA molecules synthesized by chemical methods is limited to about 100 nucleotides.

In a further step of the method according to the present invention, the RNA molecules of the population are cleaved by the catalytic nucleic acid molecule into RNA fragments (a 5' RNA fragment and at least one 3' RNA fragment) by contacting the sample resulting from the first step of the method according to the present invention with the catalytic nucleic acid molecule under conditions allowing the cleavage of the RNA molecule.

In a preferred embodiment, the catalytic nucleic acid molecule has been designed to be able to cleave the RNA molecules of the population at a specific cleavage site.

Methods to design catalytic nucleic acid molecules, in particular ribozymes that cleave RNA substrate molecules at a defined site, are known in the art.

For example, hairpin ribozymes cleave 5' of the guanosine in NGUC sequences, wherein N is any nucleotide. Furthermore, for example, a hammerhead ribozyme can be directed to cleave 3' of any NUH sequence, wherein N is any nucleotide, U is conserved, and H can be any nucleotide except G (N=G,A,C,U; H=A,C,U) (Haseloff and Gerlach, 1988. Nature 334: 585-591; McCall et al., 2000. Molecular Biotechnology 14: 5-17).

According to the substrate requirements described above, any RNA molecule can be expected to contain a number possible sites for sequence-specific cleavage by a catalytic nucleic acid molecule. In addition to the target site, the number of base pairs to be formed between the catalytic nucleic acid molecule and substrate must be chosen (substrate binding region). The affinity of a catalytic nucleic acid molecule towards its substrate can be adjusted by altering the length of the substrate binding region of the catalytic nucleic acid molecule. Although high affinity is usually desirable, an extended substrate binding region may cause problems regarding specificity and catalytic activity. Multiple turnover catalysis may be severely impaired if product release is slow due to strong binding of the target nucleic acid molecule to the catalytic nucleic acid molecule. Catalytic nucleic acid molecules with short binding arms (substrate binding region), however, may lack specificity.

The aspects to consider are catalytic activity and specificity. Catalytic nucleic acid molecules which form a larger number of base pairs with the substrate RNA are less likely to dissociate from the cleaved substrate, and therefore are not available for further cleavage. Therefore, the number of base pairs should be selected in such a way that the catalytic nucleic acid molecule-substrate complex formed is relatively stable under the conditions of the experiment, but is able to dissociate once cleavage of the substrate occurs. This typically requires 11 to 17 base pairs. For specificity, the number of base pairs formed between the catalytic nucleic acid molecule and the substrate RNA should be large enough to make the target sequence unique, but not so large that imperfectly matched substrates form stable complexes. Statistically, about 13 nucleotides are required to uniquely define a particular site in an RNA pool.

Methods for the production of catalytic nucleic acid molecules are known in the art. For example, ribozymes can be chemically synthesized using the procedure for normal RNA synthesis as described (Wincott et al., 1995. Nucleic Acids Res. 23(14):2677-84). Ribozymes can also be synthesized by in vitro transcription of suitable DNA templates using e.g. bacteriophage T7 RNA polymerase (Haseloff and Gerlach, 1988. Nature 334: 585-591).

Alternatively, in the context of the present invention, it is also envisaged that the RNA molecules of the population has been designed to have a cleavage site for the catalytic nucleic acid molecule. Methods for changing or introducing nucleotides into DNA molecules to produce specific sites are known in the art. This DNA template can then be used to produce an RNA molecule by in vitro transcription methods as explained above. These methods are known in the art.

In this context it is particularly preferred that the catalytic nucleic acid molecule is provided in trans. This means that the RNA molecules of the population and the catalytic nucleic acid molecule are not part of the same molecule. However, it is also included within the present invention that they are included in cis, i.e. the RNA molecules of the population and the catalytic nucleic acid molecule are part of the same molecule.

In a particularly preferred embodiment of the first aspect of the present invention the catalytic nucleic acid molecule is a ribozyme.

In this context it is particularly preferred that the ribozyme is selected from the group consisting of hammerhead ribozymes, hairpin ribozymes, and HDV ribozymes.

In an even more preferred embodiment, the ribozyme is a hammerhead ribozyme.

Particularly preferred in this context is a hammerhead ribozyme comprising an RNA sequence according to SEQ ID NO. 1 which can be directed to cleave 3' of any NUH sequence as shown in FIG. 5 (N=G,A,C,U; H=A,C,U) (Haseloff and Gerlach, 1988. Nature 334: 585-591; McCall et al., 2000. Molecular Biotechnology, 14: 5-17).

In an even more particularly preferred embodiment a hammerhead ribozyme HHNUH2d according to SEQ ID NO. 2 can be used which was designed to target the 5' region of the RNA sequences according to SEQ ID NO. 3-5 and shown in FIGS. 1 to 3, forming helix III with mRNA positions 1-12, and helix I with mRNA positions 14-18 (FIG. 6) of the RNA sequences according to SEQ ID No. 3-5. The 5' region of the target RNA sequence contains two possible recognition sites, NUH1 (positions 10-12) and NUH2 (positions 11-13), of which NUH2 is the preferred target site.

Sequence of the trans-acting hammerhead ribozyme
HEINUH2d (SEQ ID NO: 2):
5'-GCAUGGCUGAUGAGGCCUCGACCGAUAGGUCGAGGCCGAAAAGCUU
UCUCCC-3'

In another particularly preferred embodiment, the catalytic nucleic acid molecule is a DNAzyme, e.g. a "10-23" DNAzyme.

By the cleavage with the catalytic nucleic acid molecule, the RNA molecules of the population are cleaved at a defined site so that a 5' terminal and at least one 3' terminal RNA fragment is produced.

In the context of the present invention, the term "under conditions allowing the cleavage of the RNA molecule" means that the reaction conditions are chosen in a way to allow the binding of the catalytic nucleic acid molecule to the substrate RNA molecule and subsequent cleavage of the substrate RNA molecule. The skilled person will know which conditions can be applied in order to enable the cleavage of the substrate RNA molecule.

Two protocols are commonly used to perform the cleavage reaction. In one protocol the ribozyme and the substrate RNA are heated together at 95° C. (preferably 1 to 2 minutes) in the presence of buffer without magnesium, and subsequently cooled to the reaction temperature (20-37° C., preferably 25° C.) to promote annealing. Then MgCl$_2$ is added to initiate the cleavage reaction. In another protocol the ribozyme and substrate RNA are heated separately at 95° C. without MgCl$_2$ for one to two minutes and then cooled to the reaction temperature. $MgCl_2$ is added to both the ribozyme and the substrate RNA and the cleavage reaction is started by mixing both.

To achieve complete cleavage the $Mg^{++}$ concentration, buffer composition, pH value, temperature and reaction time may need to be adjusted.

For example, "conditions allowing the cleavage of the RNA molecule" may comprise 50-200 mM NaCl or KCl, 0.1-200 mM $Mg^{++}$, 5-100 mM Tris-HCl, pH 6.5-8.5, 20-37° C. for 5 minutes to 2 hours.

A non-ionic detergent (Tween, NP-40, Triton-X 100) can often be present, usually at about 0.001 to 2%, typically 0.05-0.2% (volume/volume).

Preferably, "conditions allowing the cleavage of the RNA molecule" mean a pH of from 6.5-7.5, preferably from 7.0-7.5, and/or a buffer concentration of from 5-100 mM, preferably from 25 to 50 mM, and/or a concentration of monovalent salts (e.g. Na or K) of from 120-170 mM, preferably 150 mM, and/or $Mg^{++}$ at a concentration of from 0.1-200 mM, preferably 20-40 mM, wherein more preferably the buffer is selected from the group consisting of Tris-HCl or HEPES.

In a further step of the method according to the present invention, the RNA fragments obtained from the cleaving step b) described above are separated.

Any suitable method for separating RNA fragments can be used, including, but not limited to denaturing gel electrophoresis or liquid chromatography.

In a particularly preferred embodiment of the first aspect of the present invention the RNA fragments are separated in step c) by denaturing gel electrophoresis or liquid chromatography, preferably HPLC, FPLC or RPLC.

Separation of RNA molecules by denaturing gel electrophoresis has been described (Maniatis et al., 1975. Biochemistry 14(17):3787-3794). For example, polyacrylamide gels that contain a high concentration of a denaturing agent such as urea are capable of resolving short (<500 nucleotides) single-stranded RNA fragments that differ in length by as little as one nucleotide. In this context polyacrylamide gels comprising 8 M urea are particularly preferred.

The RNA molecules can also be separated by liquid chromatography methods. As used herein, the term "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., the mobile phase), as this fluid moves relative to the stationary phase(s). LC includes reverse phase liquid chromatography (RPLC), high performance liquid chromatography (HPLC), high turbulence liquid chromatography (HTLC) and fast performance liquid chromatography (FPLC). In contrast to HPLC, the buffer pressure used in FPLC is relatively low, typically less than 5 bar, but the flow rate is relatively high, typically 1-5 ml/min.

Stationary phases for the use in liquid chromatography are known in the art. For example, the stationary phase can be a porous polystyrene, a porous non-alkylated polystyrene, a polystyrenedi-vinylbenzene, a porous non-alkylated polystyrenedivinylbenzene, a porous silica gel, a porous silica gel modified with non-polar residues, a porous silica gel modified with alkyl containing residues, selected from butyl-, octyl and/or octadecyl containing residues, a porous silica gel modified with phenylic residues, or a porous polymethacrylate (WO2008077592, the disclosure is incorporated herewith by reference).

In this context, ethylene-bridged hybrid organic/inorganic stationary phases are particularly preferred (Wyndham et al., 2003. Anal. Chem. 75(24):6781-8 and WO2003014450, the disclosure is incorporated herewith by reference).

For example, the separation process of RNA molecules by HPLC has been described (Weissman et al., 2013. Methods Mol. Biol. 969:43-54).

In a further step of the method of the present invention, a measure for the amount of the capped and non-capped 5' terminal RNA fragments separated in step c) described above of said population of RNA molecules is determined.

In the context of the present invention, it is necessary to determine and compare measures for the amount of the obtained capped and non-capped 5'-terminal RNA fragments. Any suitable measure can be taken including but not limited to the signal intensity of the RNA fragments.

In a preferred embodiment, the measure determined in step d) is the signal intensity of the capped and non-capped 5' terminal RNA fragments or the amount of the RNA fragments.

The signal intensity is particularly preferred, because it can be detected directly e.g. in denaturing gel electrophoresis using appropriate dyes for the staining of the RNA fragments like ethidium bromide. As explained above, it is also possible to provide the RNA fragments with an appropriate marker like a fluorescence marker or a radioactive marker and then detect the signal intensity of the marker molecule.

Alternatively, it is also included within the present invention to detect and determine the amount of the RNA fragments itself, e.g. by determining the number of RNA fragments or the mass of the RNA fragments.

In a preferred embodiment, the measure determined in step d) for the amount of the the capped and non-capped 5' terminal RNA fragments is determined by spectroscopic methods, quantitative mass spectrometry, or sequencing.

Spectroscopic methods for RNA quantification include traditional absorbance measurements at 260 nm and more sensitive fluorescence techniques using fluorescent dyes such as ethidium bromide and a fluorometer with an excitation wavelength of 302 or 546 nm (Gallagher, 2011. Quantitation of DNA and RNA with Absorption and Fluorescence Spectroscopy. Current Protocols in Molecular Biology. 93:A.3D.1-A.3D.14).

A mass spectrometer (MS) is a gas phase spectrometer that measures a parameter that can be translated into mass-to-charge ratio of gas phase ions. Examples of mass spectrometers are time-of-flight, magnetic sector, quadrupole filter, ion trap, ion cyclotron resonance, electrostatic sector analyser and hybrids of these. Methods for the application of MS methods to the characterization of nucleic acids are known in the art.

For example, Matrix-Assisted Laser Desorption/Ionization Mass Spectrometry (MALDI-MS) can be used to analyse oligonucleotides at the 120-mer level and below (Castleberry et al., 2008. Matrix-Assisted Laser Desorption/Ionization Time-of-Flight Mass Spectrometry of Oligonucleotides. Current Protocols in Nucleic Acid Chemistry. 33:10.1.1-10.1.21).

Electrospray Ionization Mass Spectrometry (ESI-MS) allows the analysis of high-molecular-weight compounds through the generation of multiply charged ions in the gas phase and can be applied to molecular weight determination, sequencing and analysis of oligonucleotide mixtures (Castleberry et al., 2008. Electrospray Ionization Mass Spectrometry of Oligonucleotides. Current Protocols in Nucleic Acid Chemistry. 35:10.2.1-10.2.19). Preferably, the mass spectrometry analysis is conducted in a quantitative manner to determine the amount of RNA.

Methods for sequencing of RNA are known in the art. A recently developed technique called RNA Sequencing (RNA-Seq) uses massively parallel sequencing to allow for example transcriptome analyses of genomes at a far higher resolution than is available with Sanger sequencing- and microarray-based methods. In the RNA-Seq method, complementary DNAs (cDNAs) generated from the RNA of interest are directly sequenced using next-generation sequencing technologies. RNA-Seq has been used successfully to precisely quantify transcript levels, confirm or revise previously annotated 5' and 3' ends of genes, and map exon/intron boundaries (Eminaga et al., 2013. Quantification of microRNA Expression with Next-Generation Sequencing. Current Protocols in Molecular Biology. 103:4.17.1-4.17.14). Consequently, the amount of the RNA fragments can be determined also by RNA sequencing.

In a further step of the method of the present invention, said measures of capped and non-capped 5' terminal RNA fragments determined as described above in step d) are compared, thereby determining the capping degree of said population of RNA molecules.

Said determination and comparison can be performed by eye or with the help of technical systems, e.g. by using computer software.

In a preferred embodiment, the ratio of capped and non-capped 5' terminal RNA fragments is calculated. In this context, reference is also made to example 3.

For example, the degrees of capped and non-capped RNA, respectively, can be calculated according to:

$$\text{capped RNA}(\%) = \frac{\text{measure capped RNA}}{\sum \text{measures}(\text{non}-\text{capped RNA} + \text{capped RNA})} \times 100$$

$$\text{non}-\text{capped RNA}(\%) = \frac{\text{measure non}-\text{capped RNA}}{\sum \text{measures}(\text{non}-\text{capped RNA} + \text{capped RNA})} \times 100$$

In a preferred embodiment, the population of RNA molecules comprises or consists of mRNA molecules.

In a preferred embodiment of the method for determining the capping degree of a population of RNA molecules having a cleavage site for a catalytic nucleic acid molecule, the orientation of the cap on a capped 5' terminal RNA fragment is further determined as described herein.

In a specific embodiment the method according to the present invention is used as a quality control in the production process of RNA molecules.

In a further aspect, the present invention also relates to the use of a catalytic acid molecule for determining the capping degree of a population of RNA molecules, wherein the catalytic acid molecule is used to cleave the RNA molecules of the population into a 5' terminal RNA fragment and at least one 3' RNA fragment with a length useful for the determination of the capping degree.

In the context of the present invention, it has been found that, as explained above, catalytic nucleic acid molecules and especially ribozymes are useful for determining the capping degree of a population of RNA molecules. Consequently, the present invention also relates to the use of said catalytic nucleic acid molecules for said purpose.

In this context in a specific embodiment the catalytic nucleic acid molecules used for determining the capping degree of a population of RNA molecules may be used in the quality control of the production process of RNA molecules.

All embodiments defined above for the method of the invention also apply in the context of said use of the invention.

In another aspect, the invention provides a novel use of a catalytic nucleic acid molecule, preferably as defined herein, in a method for analyzing an RNA molecule, preferably an mRNA molecule, more preferably a modified RNA or mRNA molecule, having a cleavage site for the catalytic nucleic acid molecule. In a preferred embodiment, a catalytic nucleic acid molecule is used for analyzing an RNA molecule as part of a quality control process during or after RNA production, wherein the RNA, preferably an mRNA molecule, more preferably a modified RNA or mRNA molecule, is preferably produced by in vitro transcription. Preferably, the catalytic nucleic acid molecule as defined herein, preferably a ribozyme, is used in a method, which comprises determining the presence or absence of a cap structure in an RNA molecule having a cleavage site for the catalytic nucleic acid molecule. Alternatively or in addition, the catalytic nucleic acid molecule as defined herein, preferably a ribozyme, is used in a method, which comprises determining the orientation of the cap structure at the 5' terminus of a capped RNA molecule, preferably an mRNA molecule.

Furthermore, the invention provides a novel use of a catalytic nucleic acid molecule, preferably as defined herein, in a method for analyzing a population of RNA molecules, wherein the population comprises at least one RNA molecule, preferably a modified RNA molecule, having a cleavage site for a catalytic nucleic acid molecule. In a preferred embodiment, a catalytic nucleic acid molecule is used according to the invention for analyzing a population of RNA molecules as part of a quality control process during or after RNA production, wherein the RNA molecules, preferably mRNA molecules, are preferably produced by in vitro transcription and wherein at least one RNA molecule has a cleavage site for the catalytic nucleic acid molecule.

In a preferred embodiment, the catalytic nucleic acid molecule is used in a method for analyzing an RNA population, wherein the population comprises at least one capped RNA molecule, preferably at least one capped modified RNA molecule, having a cleavage site for the catalytic nucleic acid molecule and wherein the method comprises determining the relative amount of capped RNA molecules having a cleavage site for the catalytic nucleic acid molecule in the population of RNA molecules. Alternatively or in addition, the catalytic nucleic acid molecule is used in a method for analyzing an RNA population, wherein the population comprises at least one correctly capped RNA molecule, preferably at least one correctly capped modified RNA molecule, having a cleavage site for the catalytic nucleic acid molecule and wherein the method comprises determining the relative amount of correctly capped RNA molecules having a cleavage site for the catalytic nucleic acid molecule in the population of RNA molecules.

In a particularly preferred embodiment, the invention concerns the use of a catalytic nucleic acid molecule, preferably as defined herein, more preferably a ribozyme, for analyzing an RNA population, preferably an mRNA population, comprising at least one RNA molecule, preferably a modified RNA molecule, having a cleavage site for the catalytic nucleic acid molecule. More preferably, the RNA population comprises at least one RNA molecule, preferably an mRNA molecule, which was produced by an in vitro transcription process. According to one embodiment, the catalytic nucleic acid molecule is used for analyzing a population of RNA molecules as part of a quality control process during or after RNA production, wherein the production preferably involves an in vitro transcription process. Therein, the population preferably comprises at least one capped RNA molecule, preferably a capped mRNA molecule, and the method is used for determining the relative amount of capped RNA molecules having a cleavage site for the catalytic nucleic acid molecule. In a particularly preferred embodiment, the method further comprises determining the relative amounts of correctly capped and reverse-capped RNA molecules, respectively, in the RNA population.

The invention further provides the use of a catalytic nucleic acid molecule in a method for analyzing an RNA molecule, wherein the method comprises at least one of the features described herein with respect to the inventive methods.

Furthermore, the invention provides a 5' terminal RNA fragment obtainable by the methods according to invention. In a preferred embodiment, the invention concerns the isolated 5' terminal RNA fragment obtainable by the methods according to invention.

In addition, the invention provides an RNA molecule consisting of 10 to 20 nucleotides, wherein the RNA molecule comprises a cap structure at its 5' terminus and the sequence NUH at its 3'-terminus, wherein N is selected from G, A, C and U; and H is selected from A, C and U.

In one embodiment, the 5' terminal RNA fragment according to the invention or the RNA molecule according to the invention comprises or consists of SEQ ID NO: 6, wherein the RNA fragment or the RNA molecule optionally comprises a cap structure at the 5' terminus.

SEQ ID NO: 6: GGGAGAAAGC

In a preferred embodiment, 5' terminal RNA fragment according to the invention or the RNA molecule according to the invention have the general structure according to the following formula:

5'-cap-$N_{10}$-NUH-3', wherein

NUH is preferably as defined above, and

N is selected from A, G, U and C.

In a preferred embodiment, $N_{10}$ in the formula above is the nucleic acid sequence defined by SEQ ID NO: 6.

Preferably, the 5' terminal RNA fragment according to the invention or the RNA molecule according to the invention comprise at least one modification as defined herein.

The invention further concerns the use of the 5' terminal RNA fragment according to the invention or the RNA molecule according to the invention in a method for analyzing an RNA molecule. In a preferred embodiment of the invention, the 5' terminal RNA fragment according to the invention or the RNA molecule according to the invention are used in a method for analyzing RNA or in a method for analyzing an RNA population, wherein the method further comprises at least one of the features as described above with respect to the inventive methods.

The invention is further explained with the help of the following figures and examples, which are intended to explain, but not to limit the present invention.

BRIEF DESCRIPTION OF THE FIGURES

The figures shown in the following are merely illustrative and shall describe the present invention in a further way. These figures shall not be construed to limit the present invention thereto.

FIG. 1: G/C optimized mRNA sequence coding for *Homo sapiens* New York Esophageal Squamous Cell Carcinoma 1 antigen (HsNY-ESO-1; SEQ ID NO: 3).

FIG. 2: G/C optimized mRNA sequence coding for *Photinus pyralis* Luciferase (PpLuc; SEQ ID NO: 4).

FIG. 3: G/C optimized mRNA sequence coding for *Homo sapiens* prostate stem cell antigen (HsPSCA; SEQ ID NO: 5).

FIGS. 4A-B: Schematic diagram of non-capped (A) and capped mRNA (B).

FIGS. 7A-B: Separation of capped and non-capped RNA fragments by denaturing polyacrylamide gel electrophoresis (dPAGE). RNAs were synthesized in the absence (−) or presence (+) of a cap analog as described in Example 2 and subsequently incubated without (−) or with (+) hammerhead (HH) ribozyme HHNU2d as described in Example 3. (A) Full gel and (B) enlarged part of gel with capped and non-capped RNA fragments.

(A) Full chromatogram showing the separation of the hammerhead (HH) ribozyme from the 3' mRNA fragment.

(B) Enlarged area of the chromatogram showing the separation of capped and non-capped 5' mRNA fragments.

FIGS. 9A-D: Resolution of co-transcriptionally capped, non-capped, and enzymatically capped 5' mRNA fragments separated by dPAGE and HPLC. *Photinus pyralis* luciferase (PpLuc) RNAs were synthesized in the absence (no cap) or presence (cotx) of a cap analog, non-capped RNAs were subsequently enzymatically capped (Ecap) as described in Example 2. The RNAs were incubated with hammerhead (HH) ribozyme HHNU2d as described in Example 3 and analysed by dPAGE and HPLC.

(A) Enlarged part of a dPAGE gel with capped (cotx, Ecap) and non-capped (no cap) RNA fragments. Two bands were detected for co-transcriptionally capped RNA.

(B-D) Enlarged area of the HPLC chromatogram showing the separation of capped and non-capped 5' mRNA fragments. (B) Non-capped PpLuc RNA, (C) enzymatically capped PpLuc RNA originating from (B), (D) co-transcriptionally capped PpLuc RNA. Five peaks were detected for co-transcriptionally capped mRNA.

Figure 10:
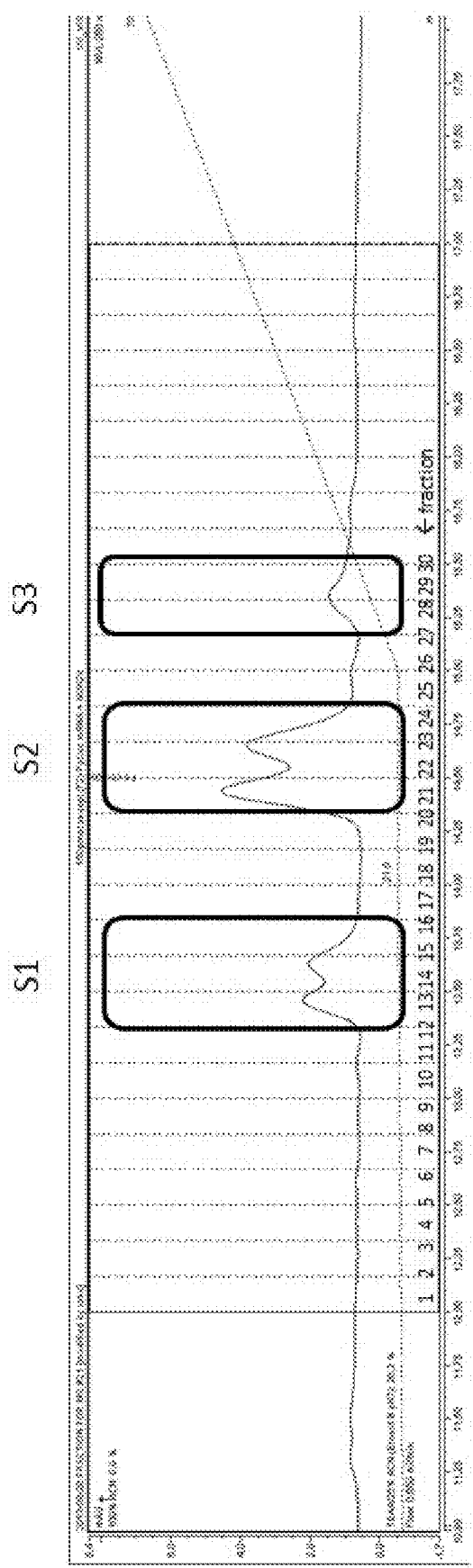

FIG. 10: Fractionation of co-transcriptionally capped 5' mRNA fragments via HPLC. *Photinus pyralis* luciferase (PpLuc) RNAs were synthesized in the presence of a cap analog as described in Example 2, incubated with hammerhead (HH) ribozyme HHNU2d as described in Example 3, and analyzed via HPLC. Fractions were collected over the course of time as indicated on the x-axis of the diagram.

Double peaks at 13.30-13.80 minutes and 14.30-14.80 minutes could not be separated via HPLC and were thus pooled prior to MALDI analysis (sample S1=fractions 12-14, S2=21-24, S3=28-30).

FIGS. 11A-B: MALDI-TOF spectrum for samples S1 and S2 obtained after HPLC separation of ribozyme-cleaved 5' terminal RNA fragments of co-transcriptionally capped *Photinus pyralis* luciferase (PpLuc) RNAs. Analyses were performed as described in Example 3.

FIGS. 12A-D: Overlay of HPLC analyses of co-transcriptionally capped, non-capped, and enzymatically capped 5' terminal RNA fragments. *Photinus pyralis* luciferase (PpLuc) RNAs were synthesized in the absence (no cap) or presence of a cap analog, non-capped RNAs were subsequently enzymatically capped (Ecap) as described in Example 2. In addition, enzymatically capped *Photinus pyralis* Luciferase (PpLuc) RNAs lacking the initial 5' guanosine (Ecap-G1) were synthesised analogously. The RNAs were incubated with hammerhead (HH) ribozyme HHNU2d as described in Example 3 and analysed by HPLC.

FIGS. 13A-D: Quantitation of different RNA populations. Peak areas (mAU*min) for non-capped, correctly capped and reverse-capped RNA populations (FIG. 12 D, full-length and minus1G ('n-1') RNA) were determined using Chromeleon software. Relative proportions were plotted: (A) distribution of single populations; (B) combined capped versus non-capped populations; (C) combined minusG1 RNA (correctly capped and reverse-capped) and combined full-length RNA (correctly capped and reverse-capped) versus non-capped; (D) combined correctly capped RNA (full-length and minus1G), combined reverse-capped RNA (full-length and minusG1) versus non-capped RNA.

EXAMPLES

The examples shown in the following are merely illustrative and shall describe the present invention in a further way. These examples shall not be construed to limit the present invention thereto.

Example 1

Preparation of Hammerhead Ribozymes

Figure 5:
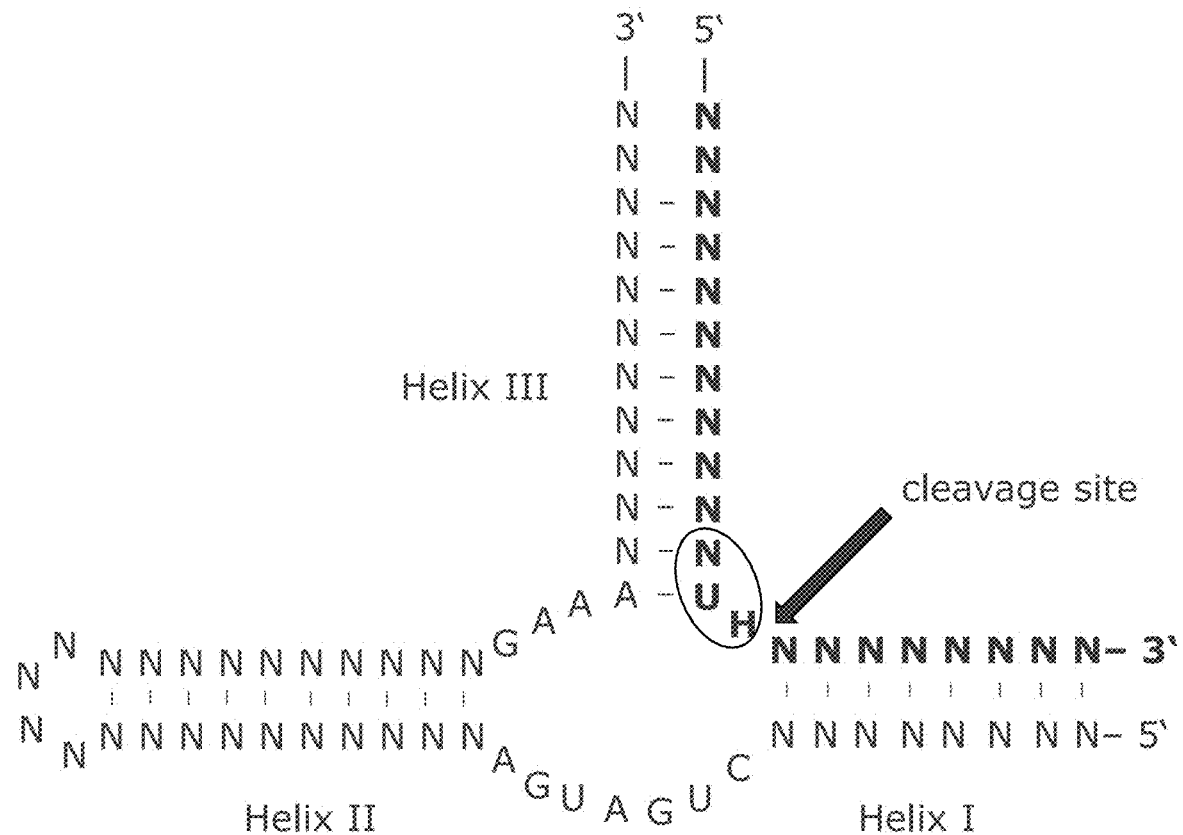
FIG. 5: Diagram of hammerhead ribozyme annealed to target RNA sequence (highlighted in bold).

1. A hammerhead ribozyme can be directed to cleave 3' of any NUH sequence as shown in FIG. 5 (N=G,A,C,U; H=A,C,U) (Haseloff and Gerlach, 1988. Nature 334: 585-591; McCall et al., 2000. Molecular Biotechnology 14: 5-17). The schematic diagram of FIG. 5 shows how helix I and helix III anneal to the target RNA sequence.

Figure 6:
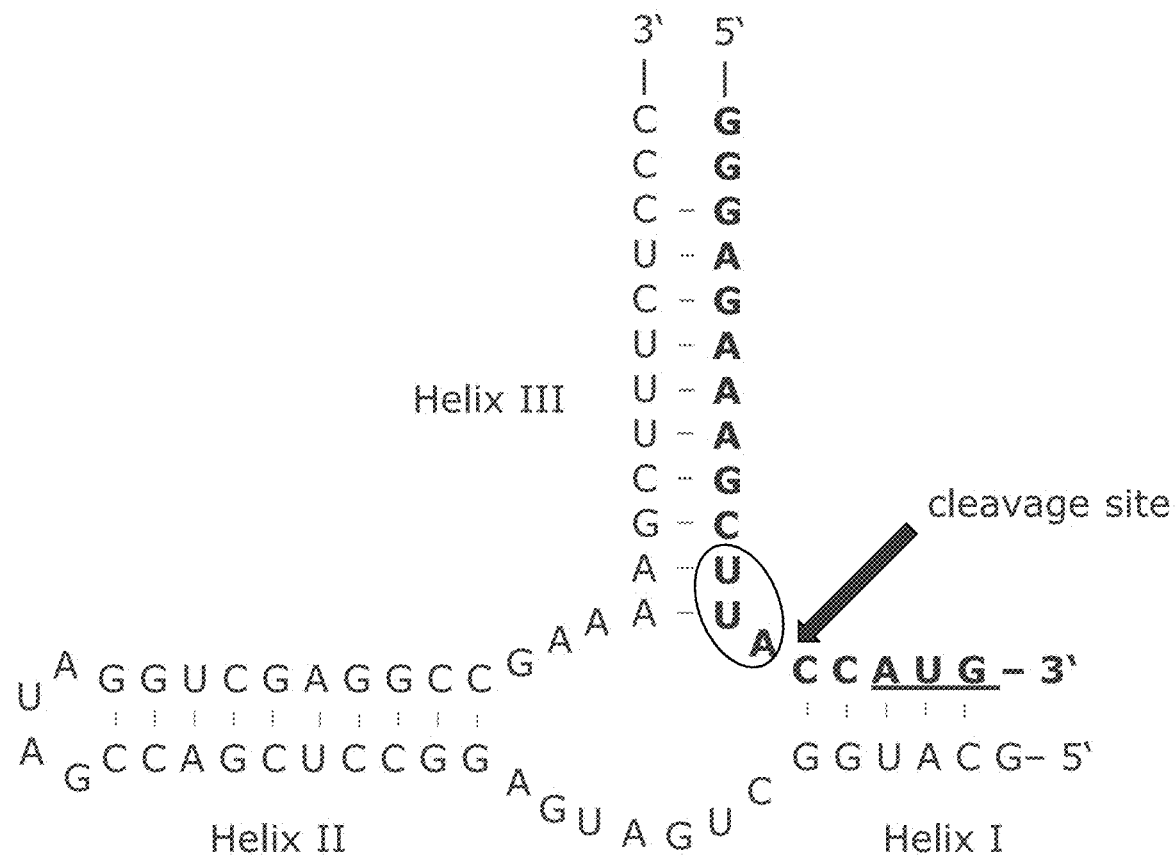
FIG. 6: Hammerhead ribozyme HHNUH2d annealed to 5' UTR of target mRNA sequence (highlighted in bold). Recognition site marked by circle and AUG start codon underlined. Cleavage at the indicated site yields a 13 mer 5' fragment of non-capped RNA (or a 14 mer fragment if the RNA is capped).

2. The trans-acting hammerhead ribozyme HHNUH2d was designed to target the 5' region of the RNA sequences shown in FIGS. 1 to 3, forming helix III with mRNA positions 1-12, and helix I with mRNA positions 14-18 (FIG. 6). The 5' region of the target RNA sequence contains two possible recognition sites, NUH1 (positions 10-12) and NUH2 (positions 11-13), of which NUH2 is the preferred target site.

```
Sequence of the trans-acting hammerhead ribozyme
HHlNUH2d (SEQ ID NO: 2):
5'-GCAUGGCUGAUGAGGCCUCGACCGAUAGGUCGAGGCCGAAAAGCUU
UCUCCC-3'
```

3. The ribozyme HHNUH2d was synthesized and HPLC purified by Biomers.net GmbH (Ulm, Germany), and 200 µg were resolved on a preparative denaturing 10 cm×8 cm×1.0 mm acrylamide gel for purification (8 M urea (Applichem), 20% acrylamid:bisacrylamid 19:1 (Applichem), 1×TBE, 1% APS (AppliChem), 0.1% TEMED (AppliChem); 180 V, 2 hours, Mini-PROTEAN® Tetra Cell (BioRad)). The ribozyme band was identified by UV shadowing (E-BOX VX2 gel documentation system with 312 nm-UV Transilluminator (Peqlab)) over a TLC plate (Kieselgel 60 F254, Merck), excised and eluted from the gel slice in 10 mM Tris/HCl, pH 7.5 (room temperature, 16 hours). The supernatant was filtered through Corning® Costar® Spin-X columns (Sigma) (1 minute, 16.000 g, room temperature), and RNAs were precipitated (300 mM NaOAc, pH 5, 75% ethanol, 16 hours, −20° C.). Following centrifugation (30 minutes, 16.000 g, 4° C.), pellets were washed in 75% ethanol (invert, centrifuge 5 minutes, 16.000 g, 4° C.), dried and re-dissolved in $H_2O$.

Example 2

Preparation of the mRNA

1. Preparation of DNA and mRNA Constructs

For the present example DNA sequences encoding HsNY-ESO-1 mRNA according to SEQ ID NO: 3 (FIG. 1), PpLuc mRNA according to SEQ ID NO: 4 (FIG. 2) and HsPSCA RNA according to SEQ ID NO: 5 (FIG. 3) were prepared and used for subsequent in vitro transcription reactions.

According to a first preparation, the DNA sequences coding for the above mentioned mRNAs were prepared. The constructs were prepared by modifying the wild type coding sequence by introducing a GC-optimized sequence for stabilization, followed by a stabilizing sequence derived from the alpha-globin-3'-UTR (muag (mutated alpha-globin-3'-UTR)), a stretch of 64 adenosines (poly-A-sequence), a stretch of 30 cytosines (poly-C-sequence), and a histone stem loop. In FIGS. 1 to 3 the sequences of the corresponding mRNAs are shown.

The 5' region of the target RNA sequence contains two possible recognition sites, NUH1 (positions 10-12) and NUH2 (positions 11-13), of which NUH2 is the preferred target site. Cleavage occurs 3' the H of the NUH recognition site.

2. In Vitro Transcription

The respective DNA plasmids prepared according to paragraph 1 were transcribed in vitro using T7 RNA polymerase.

3. In Vitro Transcription in the Presence of Cap Analog

For the production of 5'-capped RNAs using cap analog, transcription was carried out in 5.8 mM m7G(5')ppp(5')G Cap analog, 4 mM ATP, 4 mM CTP, 4 mM UTP, and 1.45 mM GTP (all Thermo Fisher Scientific).

4. In Vitro Transcription of Non-Capped RNAs

For the production of non-capped, 5' triphosphate RNAs, transcription was carried out in the presence of 4 mM of each ATP, GTP, CTP and UTP (all Thermo Fisher Scientific).

5. Enzymatic Capping of mRNA

Enyzmatic capping was performed using the ScriptCap™ $m^7G$ Capping System (Cell Script) according to the manufacturer's instructions. In brief, per reaction, 60 µg of non-capped RNAs were heat-denatured (10 minutes, 65° C.) in a volume of 68.5 µl and immediately cooled on ice (5 minutes). Following addition of reaction components (1× ScriptCap Capping buffer, 1 mM GTP, 0.1 mM SAM, 1000 U/ml ScripGuard RNase Inhibitor, 400 U/ml ScriptCap Capping Enzyme) to a final volume of 100 µl, reactions were incubated for 1 hour at 37° C. RNAs were precipitated in 2.86 M LiCl for 16 hours at −20° C., followed by centrifugation (30 minutes, 16.000 g, 4° C.). Pellets were washed in 0.5 reaction volumes 75% ethanol (invert, centrifuge 5 minutes, 16.000 g, 4° C.), dried and re-dissolved in H₂O.

Subsequently the mRNA was purified using PureMessenger® (CureVac, Tubingen, Germany; WO2008/077592A1).

TABLE 2

Target RNAs

| Description (Name) | Length of Sequence (nucleotides) | SEQ ID NO | Experiment |
|---|---|---|---|
| HsNY-ESO-1 mRNA | 760 | 3 | Capped mRNA (used for PAGE, FIG. 7) |
| PpLuc mRNA | 1870 | 4 | co-transcriptionally capped mRNA (used for HPLC/PAGE) |
| PpLuc mRNA | 1870 | 4 | enzymatically capped mRNA (used for HPLC/PAGE) |
| PpLuc mRNA | 1870 | 4 | non-capped RNA (used for HPLC/PAGE as no cap control) |
| HsPSCA mRNA | 589 | 5 | non-capped RNA (used for PAGE, FIG. 7 as no cap control) |

Example 3

Cap Analysis Assay

1. Principle of the Assay

The hammerhead ribozyme HHNUH2d of example 1 was incubated with the in vitro transcribed RNAs of example 2 (Table 2) and the cleavage products were separated by denaturing polyacrylamide gel electrophoresis (PAGE) or high performance liquid chromatography (HPLC).

2. Ribozyme Cleavage Reaction

Reaction scales for gel analysis were usually 1× (10 pmol RNA). For HPLC analysis, 15× reaction (150 pmol RNA) were set up, allowing a more sensitive detection and thus a more precise determination of the respective mRNA populations. Per reaction, 10 pmol of HHNUH2d and 10 pmol of the respective substrateRNA were annealed in 0.625 mM EDTA in a total volume of 6 µl (2 min at 95° C., 0.1° C./sec to 25° C., 10 min at 25° C.). After addition of 4 µl of 100 mM MgCl₂, 125 mM Tris/HCl, pH 7.5 (final concentration 40 mM MgCl₂, 50 mM Tris/HCl), the reaction was incubated at 25° C. for 1 hour. For analysis via polyacrylamide gel electrophoresis (PAGE), the 1× reaction was stopped with 30 µl 95% formamide, 20 mM EDTA. For HPLC analysis, the 15× reaction was stopped with 24 µl 250 mM EDTA (final concentration 40 mM).

3. Gel Separation, Quantification of Cleavage Products and Calculation of Capping Degree Stopped reactions were heat-denatured (heated to 80° C. for 2 minutes, immediately put on ice for 5 minutes) and separated on a 10 cm×8 cm×1.5 mm 20% denaturing PAGE (8 M urea (AppliChem), 20% acrylamid:bisacrylamid 19:1 (AppliChem), 1×TBE, 1% APS (AppliChem), 0.1% TEMED (AppliChem); 180 V, 2 hours, Mini-PROTEAN® Tetra Cell (BioRad)). Gels were stained for 10 minutes in 1:10,000 SYBR Gold (Invitrogen) in TBE and documented on a E-BOX VX2 gel documentation system with 312 nm-UV Transilluminator (Peqlab) (excitation maximum for SYBR Gold: ~300 nm, emission: ~537 nm).

To determine the capped proportion in the mRNA preparations, bands of the respective 13-mer (derived from the non-capped fraction) or 14-mer (derived from the capped fraction) cleavage products can be quantified using Quantity One 1-D Analysis Software (BioRad).

The degrees of capped and non-capped RNA, respectively, can be calculated according to:

$$\text{capped RNA}(\%) = \frac{\text{signal intensity 14mer}}{\sum \text{signal intensities}(13mer + 14mer)} \times 100$$

$$\text{non-capped RNA}(\%) = \frac{\text{signal intensity 13mer}}{\sum \text{signal intensities}(13mer + 14mer)} \times 100$$

As can be seen in FIG. 7, the capped and uncapped RNA fragments produced by ribozyme cleavage of long mRNA molecules can be resolved by denaturing PAGE.

4. HPLC Separation, Quantification of Cleavage Products and Calculation of Capping Degree For the experiment shown in FIG. 8 an mRNA sample was prepared by mixing 60% enzymatically capped mRNA coding for *Photinus pyralis* Luciferase (PpLuc) and 40% non-capped mRNA coding for *Photinus pyralis* Luciferase (PpLuc). Subsequently this sample was incubated with the hammerhead (HH) ribozyme HHNU2d as described above and analysed by HPLC.

Analysis was performed via ion-pair, reversed-phase chromatography on a Dionex Parallel-HPLC U3000 CV-P-1247, equipped with analytical pump (DPG-3600SD), column oven (TCC-3000SD) and UV/Vis-4-channel-detectors (2×VWD-3400RS) with analytical SST measuring cell (11 µL, 10 mm, for VWD-3×00 detector). An AQUITY UPLC OST C18 column (2.1×50 mm, 1.7 µm particle size; Waters Corporation, Milford, Mass., USA) was used. Column temperature was set to 60° C. Buffer A contained 0.1 M triethylammonium acetate (TEAA), pH 6.8, buffer B 0.1 M TEAA, pH 7.3, 25% acetonitrile. The column was equilibrated with 14% buffer B.

For sample preparation, HPLC equilibration buffer (86% buffer A, 14% buffer B) was added to the stopped hammerhead ribozyme reactions to obtain a final volume of 1700 µl.

1650 µl of the RNA solution were loaded using a SEMI-PREP-Autosampler (WPS-3000SL, Dionex) and run with a stepped gradient beginning with 14% buffer B for 3 minutes, increasing to 19% buffer B over 2 minutes, to 21% buffer B over 9 minutes. 21% buffer B was held for 1 minute, then increased to 100% B over 5 minutes, held for 3.5 minutes, then decreased to 14% buffer B over 1.5 minutes.

Signal integration was done using Chromeleon software 6.80 SR11 Build 3161 (Dionex). The relative peak areas of capped 5' RNA fragment (Peak 1, FIG. 8B) and non-capped 5' RNA fragments (Peak 2, FIG. 8B) were determined. The degree of capped RNA was calculated by dividing the relative peak area of Peak 1 by the sum of peak areas 1 and 2. Deviation from the expected capping degree was determined by dividing the calculated capping degree by the expected capping degree.

TABLE 3

Determination of capping degree after HPLC separation of cleavage products

| % capped expected | Relative peak area Peak 1 capped | Relative peak area Peak 2 non-capped | % capped calculated | % Deviation calculated/ expected |
|---|---|---|---|---|
| 60 | 67.6 | 32.4 | 67.6 | 12.7 |

Figure 8A:
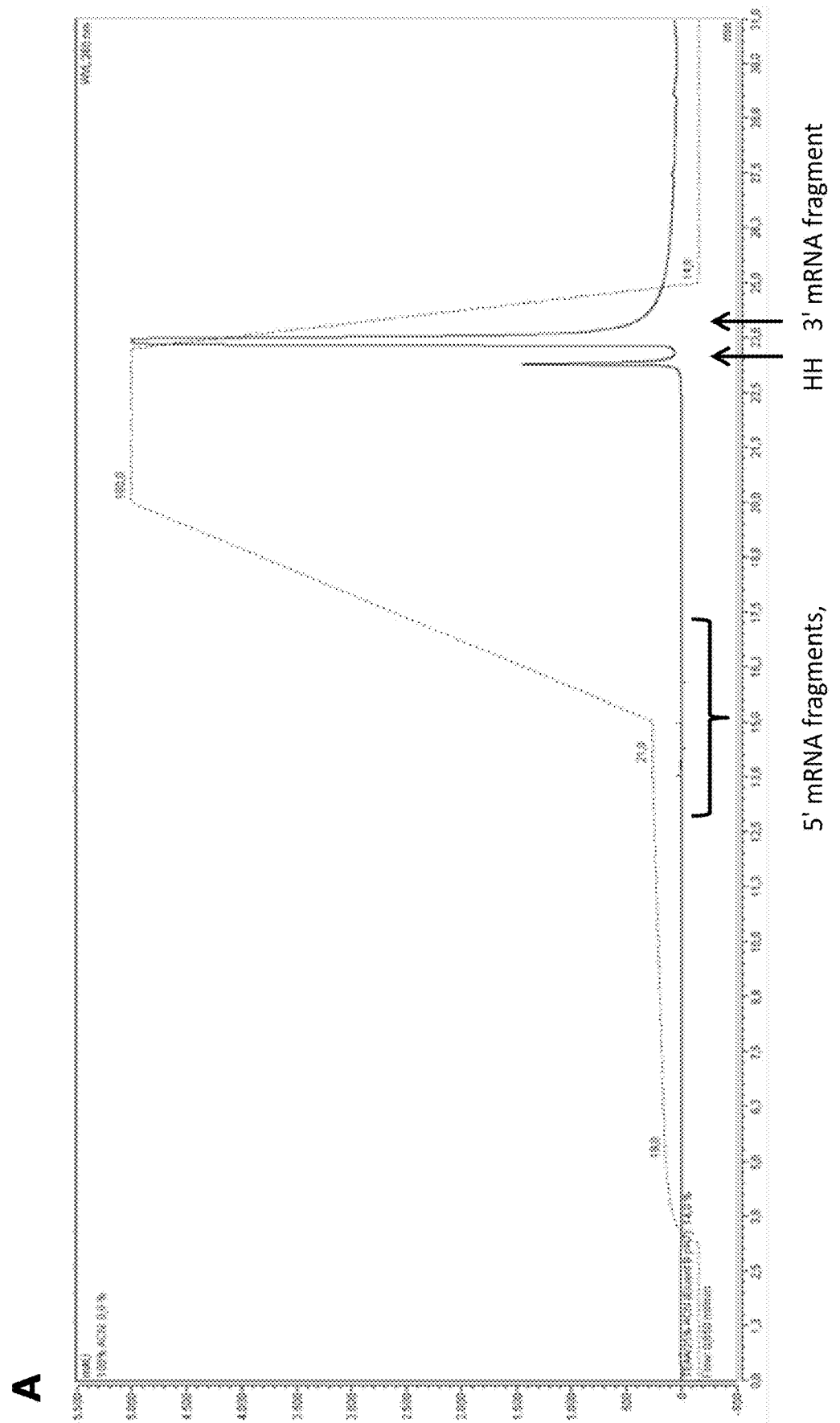
FIGS. 8A-B: Separation of capped 5' mRNA fragments, non-capped 5' mRNA fragments, 3' mRNA fragments and hammerhead ribozyme by HPLC. The mRNA sample was prepared by mixing 60% enzymatically capped mRNA coding for *Photinus pyralis* Luciferase (PpLuc) and 40% non-capped mRNA coding for *Photinus pyralis* Luciferase (PpLuc). Subsequently, this sample was incubated with the hammerhead (HH) ribozyme HHNU2d as described in Example 3 and analysed by HPLC.
Figure 8B:
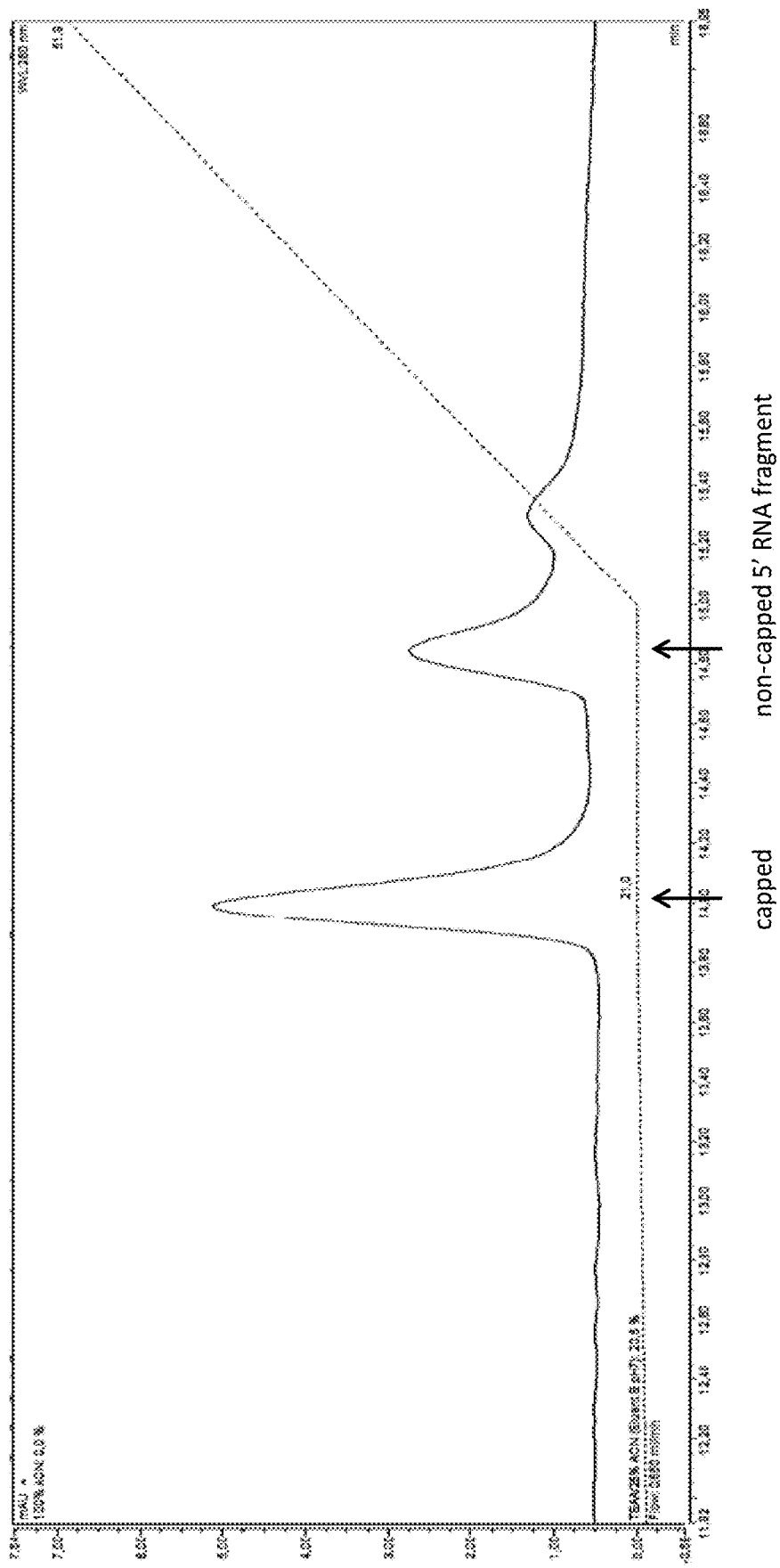

As can be seen from FIG. 8, the capped 5' mRNA fragment, non-capped 5' mRNA fragment, 3' mRNA fragment and hammerhead ribozyme can be separated by HPLC and the capping degree was calculated as explained above.

Example 4

Determination of Cap Orientation

For the experiment shown in FIG. 9, non-capped, enzymatically capped and co-transcriptionally capped RNA samples encoding *Photinus pyralis* luciferase (PpLuc) were prepared as described in Example 2. Subsequently, these samples were incubated with the hammerhead (HH) ribozyme HHNU2d as described in Example 3 and analysed in parallel by denaturing polyacrylamide gel electrophoresis (dPAGE) and HPLC. On the dPAGE gel, two bands are detected for co-transcriptionally capped RNA (FIG. 9A), whereas five peaks are detected in the HPLC chromatogram for the same sample (FIG. 9D).

In order to characterize the peaks in the HPLC chromatogram shown in FIG. 9, they were separated by HPLC according to the protocol described above and collected (fraction collection by time: 12-17 min, 20 sec/fraction) (FIG. 10). Double peaks at 13.30-13.80 min and 14.30-14.80 min could not be separated and were thus pooled prior to Matrix-assisted laser desorption/ionization (MALDI-TOF) analysis (sample S1=fractions 12-14, S2=21-24, S3=28-30). MALDI-TOF mass spectrometry was performed by using an AnchorChip target at the service provider PANAteqs (Heilbronn, Germany).

Whereas two double peaks were detected by HPLC (FIG. 10), mass spectrometry only revealed a single mass (in addition to minor salt adducts) for each double peak (FIG. 11), corresponding to the expected capped 5' fragment (FIG. 10 Peak S2, FIG. 11B) and a further double peak (FIG. 10 Peak S 1, FIG. 11A), respectively. Double peak S1 indicated a capped RNA population lacking one nucleotide in the 5' terminal RNA fragment. It was speculated that in vitro transcription from the template used in Example 2 (SEQ ID NO: 2, see FIG. 2) does not only yield the desired full-length transcript, but also an aberrant transcript lacking the 5' terminal guanine nucleotide of SEQ ID NO: 2. It was further speculated that double peak S1 in the chromatogram of FIG. 9 was derived from said aberrant transcripts.

To verify the mass spectrometry results indicating a capped 5' terminal RNA fragment derived from an RNA population lacking one guanosine phosphate, enzymatically capped *Photinus pyralis* luciferase (PpLuc) RNAs lacking the 5' terminal guanosine (Ecap-G1) were synthesized as described above. The RNAs were incubated with hammerhead (HH) ribozyme HHNU2d as described in Example 3 and analysed by HPLC.

Overlay of the chromatograms of co-transcriptionally capped RNA and the control construct Ecap(-G1) confirmed the MALDI results (FIG. 12), identifying double peak S1 in the chromatogram of FIG. 9 as RNA shortened by one guanosine at the 5' end, i.e. lacking the first G nucleotide in SEQ ID NO: 2. Therein, the first peak of the first double peak (S1) co-eluted with the enzymatically capped shortened control molecule (Ecap(-G1)). Likewise, the first peak of the second double peak (S2) eluted simultaneously with the enzymatically capped control (Ecap), again confirming the MALDI results.

In enzymatically capped RNA, the cap is present in the correct orientation ("correctly capped"). As confirmed by the simultaneous elution of the first peak of the double peaks with the capped controls (Ecap and Ecap(-G1), respectively), the respective first peaks thus correspond to correctly capped RNA. The respective second peaks correspond to those RNA molecules, which have, in contrast, incorporated the cap in the reverse orientation ("reverse-capped"). The reverse-capped fractions displayed delayed elution due to higher hydrophobicity at the 5' end (Dickman, 2011. Ion Pair Reverse-Phase Chromatography: A Versatile Platform for the Analysis of RNA. Chromatography Today, March 2011, p. 22-26). The capping degree for the different populations was calculated as explained above (FIG. 13).

TABLE 4

Determination of the relative amounts of correctly capped, reverse-capped and non-capped RNA populations after HPLC separation of cleavage products of co-transcriptionally produced mRNA

| RNA population | % of total RNA |
| --- | --- |
| Correct cap minusG1 | 13.0 |
| Reverse cap minusG1 | 14.2 |
| Correct cap full-length | 28.8 |
| Reverse cap full-length | 38.0 |
| No cap | 6.1 |

The invention claimed is:

1. A method for analyzing the cap structure at the 5' terminus of an RNA molecule having a cleavage site for a catalytic nucleic acid molecule, the method comprising the steps of:
   a) providing an RNA molecule having a cleavage site for a catalytic nucleic acid molecule,
   b) denaturing the RNA molecule, annealing the denatured RNA molecule with the catalytic nucleic acid molecule under conditions allowing cleavage of the denatured RNA molecule to produce a 5' terminal RNA fragment and at least one 3' RNA fragment, and
   c) determining the presence a cap structure at the 5' terminus of the RNA molecule.

2. The method of claim 1, further comprising separating the RNA fragments obtained in step b).

3. The method of claim 2, wherein the RNA fragments are separated by denaturing gel electrophoresis or liquid chromatography.

4. The method of claim 3, wherein liquid chromatography comprises high performance liquid chromatography, fast protein liquid chromatography, or reverse phase liquid chromatography.

5. The method of claim 1, wherein the catalytic nucleic acid molecule has a specific cleavage site.

6. The method of claim 1, wherein the cleavage site for the catalytic nucleic acid molecule is located within 50 nucleotides of the 5' terminus of the RNA molecule.

7. The method of claim 1, wherein the catalytic nucleic acid molecule is a ribozyme.

8. The method of claim 7, wherein the ribozyme is a hammerhead ribozyme, a hairpin ribozyme, or an hepatitis delta virus ribozyme.

9. The method of claim 1, wherein the RNA molecule is generated by in vitro transcription.

10. The method of claim 9, wherein the in vitro transcription is carried out in the presence of a cap analog.

11. The method of claim 10, wherein the cap analog is selected from the group consisting of G[5']ppp[5']G, $m^7$G [5']ppp[5']G, $m_3^{2,2,7}$G[5']ppp[5']G, $m_2^{7,3'-O}$G[5']ppp[5']G (3'-ARCA), $m_2^{7,2'-O}$GpppG (2'-ARCA), $m_2^{7,2'-O}$GppspG D1 (β-S-ARCA D1) and $m_2^{7,2'-O}$GppspG D2 (β-S-ARCA D2).

12. The method of claim 9, wherein the in vitro transcribed RNA molecule is enzymatically capped.

13. The method of claim 1, wherein the RNA molecule is an mRNA molecule.

14. The method of claim 1, wherein the RNA molecule comprises at least one modification.

15. The method of claim 1, wherein determining comprises comparing a structural feature or a physical parameter of the cap structure with that of a reference RNA fragment.

16. The method of claim 1, wherein step c) comprises spectroscopic analysis, quantitative mass spectrometry, or sequencing.

17. The method of claim 1, wherein determining comprises determining the orientation of a cap on the 5' terminus of the RNA molecule.

* * * * *

UNITED STATES PATENT AND TRADEMARK OFFICE
CERTIFICATE OF CORRECTION

PATENT NO. : 10,648,017 B2
APPLICATION NO. : 15/195901
DATED : May 12, 2020
INVENTOR(S) : Wochner It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 637 days.

Signed and Sealed this
Thirteenth Day of December, 2022

Katherine Kelly Vidal
*Director of the United States Patent and Trademark Office*